US007524946B2

(12) United States Patent
Howe

(10) Patent No.: US 7,524,946 B2
(45) Date of Patent: Apr. 28, 2009

(54) **NUCLEIC ACIDS ENCODING *SARCOCYSTIS NEURONA* ANTIGEN AND USES THEREOF**

(75) Inventor: Daniel K. Howe, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 78 days.

(21) Appl. No.: 11/774,830

(22) Filed: Jul. 9, 2007

(65) Prior Publication Data

US 2008/0214484 A1    Sep. 4, 2008

Related U.S. Application Data

(63) Continuation of application No. 11/445,045, filed on Jun. 1, 2006, now Pat. No. 7,256,282.

(51) Int. Cl.
*C07H 21/04* (2006.01)
(52) U.S. Cl. .................. 536/23.7; 435/320.1; 536/24.1; 536/24.2; 536/24.32
(58) Field of Classification Search ............. 435/320.1; 536/23.7, 24.1, 24.2, 24.32
See application file for complete search history.

(56) References Cited

U.S. PATENT DOCUMENTS 6,808,714 B2 * 10/2004 Dame et al. .............. 424/269.1

* cited by examiner

*Primary Examiner*—Jennifer E Graser
(74) *Attorney, Agent, or Firm*—King & Schickli, PLLC

(57) ABSTRACT

The present invention provides novel isolated nucleic acids encoding antigenic proteins derived from *Sarcocystis neurona,* or unique fragments thereof. In particular, the invention provides novel isolated nucleic acids encoding membrane-associated polypeptides SnSAG2, SnSAG3, and SnSAG 4. Also provided are purified antigenic polypeptide fragments encoded by the novel nucleic acid sequences set forth herein that encode for SnSAG2, SnSAG3, and SnSAG 4. Also provided are isolated nucleic acids capable of selectively hybridizing with the nucleic acid from *Sarcocystis neurona.* The invention also provides vectors comprising the nucleic acids of the invention encoding an antigenic protein derived from *Sarcocystis neurona* or a unique fragment thereof and provides the vector in a host capable of expressing the polypeptide encoded by that nucleic acid. Finally, the invention provides purified polyclonal and/or monoclonal antibodies specifically reactive with *Sarcocystis neurona* and a method of detection of *Sarcocystis neurona* utilizing the antibodies of the invention.

17 Claims, 8 Drawing Sheets

FIG. 2

NUCLEIC ACIDS ENCODING *SARCOCYSTIS NEURONA* ANTIGEN AND USES THEREOF

The present application is a continuation of U.S. utility patent application Ser. No. 11/445,045, filed on Jun. 1, 2006 now U.S. Pat. No. 7,256,282, which in turn claims priority to U.S. utility patent application Ser. No. 10/369,430, filed on Feb. 19, 2003, which claims the benefit of priority of U.S. provisional patent application No. 60/357,479, filed Feb. 15, 2002, the disclosures of each of which are incorporated herein in their entirety by reference.

TECHNICAL FIELD

The present invention relates to nucleic acids of *Sarcocystis neurona*. In particular, the present invention relates to nucleic acids of *Sarcocystis neurona* and to nucleic acid reagents and antibodies for use in methods of detection and prevention of *Sarcocystis neurona* infection. More particularly, the present invention relates to novel nucleic acid sequences of *Sarcocystis neurona* and to utilization thereof including primers, probes, antigen/antibody diagnostic kits, vectors for production of peptides encoding the novel nucleic acids, and to antigenic proteins and vaccines against *Sarcocystis neurona*.

BACKGROUND OF THE INVENTION

*Sarcocystis neurona* is an apicomplexan parasite that is the primary cause of equine protozoal myeloencephalitis (EPM; Dubey et al., 1991), which is a common and debilitating infectious disease that affects the central nervous system of horses. *S. neurona* is related to the human and animal pathogen *Toxoplasma gondii* and to the important veterinary pathogen *Neospora* spp. The geographic range of *S. neurona* appears to be limited to the western hemisphere, thus EPM primarily affects horses in the Americas.

Definitive antemortem diagnosis of EPM remains exceedingly difficult, for a variety of reasons. Horses afflicted with EPM exhibit signs that are similar to a number of different neurological disorders (MacKay et al., 2000). Furthermore, *S. neurona* infection does not equate to disease, since only a small proportion of seropositive horses will suffer from EPM (MacKay et al., 2000); as a consequence, the detection of anti-*S. neurona* antibodies in serum provides little diagnostic information other than indicating previous exposure to the parasite. Analysis of cerebrospinal fluid (CSF) to reveal intrathecal antibody production has improved the predictive value of antibody detection for EPM diagnosis. However, interpretation of CSF antibody presence can be confounded by contamination of the CSF sample with minute amounts of serum antibodies (Miller et al., 1999).

Other contemporary diagnostic assays provide only mediocre predictive value for EPM diagnosis. Western blot analysis (a.k.a., immunoblot) of crude *S. neurona* lysate remains the principal immunodiagnostic test that is used to detect antibodies in suspect EPM horses (Granstrom et al., 1993). The assay relies on the recognition of several antigens, primarily in the low molecular weight range, by serum/CSF antibodies (Dubey et al., 2001b; Granstrom et al., 1993; MacKay et al., 2000). Unfortunately, Western blot analysis is primarily a research tool that is relatively laborious and somewhat hindered by subjectivity, so any improvements to the immunoblot are of limited value. While the immunoblot has been utilized for a number of years to help diagnose EPM, it is a first-generation test that needs to be replaced with improved assays based on simplified, and thus more reliable, techniques that are more appropriate for diagnostic use.

Nucleic acid amplification assays (polymerase chain reaction; PCR) for *S. neurona* detection have been developed based on the *S. neurona* ribosomal RNA genes (Fenger et al., 1994; Marsh et al., 1996). These PCR-based assays detect the presence of *S. neurona* DNA, and therefore the parasite, in the horse, so they can provide a definitive indication of active infection. However, prior to the present invention, these nucleic acid-based tests have been inherently unreliable. Specifically, parasites may be very few or non-existent in a CSF sample, so there will be few or no available target molecules (i.e., parasite genomic DNA) for PCR amplification. More importantly, the general use of PCR for diagnosis is still suspect. Although measures can be taken to improve the reliability of PCR, the technique continues to be troubled by both false positive and false negative results.

The selection of an antigen for development of a diagnostic test can be somewhat subjective since any particular pathogen is composed of numerous antigenic proteins. Logically, the target molecule in a diagnostic assay must elicit a detectable antibody response in the infected animal. In this regard, surface antigens of the Coccidia, such as the primary surface antigens of *Toxoplasma gondii* (Handman and Remington, 1980; Sharma et al., 11983) and *Neospora caninum* (Howe et al., 1998), are exceedingly immunogenic. These surface antigens have been designated SAGs and SAG-related sequences (SRSs). Significantly, the TgSAG1 surface antigen of *T. gondii* has been shown to protect mice against acute toxoplasmosis (Bulow and Boothroyd, 1991), and the NcSAG1 (p29) major surface antigen of *N. caninum* has been used to develop an ELISA for detection of *Neospora* infection in cattle (Howe et al., 2002). Collectively, these previous studies demonstrate that coccidian SAGs are at least candidate proteins for the development of both diagnostic assays and protective vaccines.

Despite the foregoing art, prior to the present invention it had not been shown that the surface antigens of *S. neurona* (i.e., SnSAG2, SnSAG3, and SnSAG4) are effective target molecules for examining immune responses in infected horses and for developing improved assays for EPM diagnosis. Such molecules would also provide the basis for improved vaccines and diagnostic kits, including antigen and antibody kits, for fast and reliable diagnosis of *S. neurona* infection.

SUMMARY OF THE INVENTION

The present invention satisfies the aforementioned need in the art by providing a novel isolated nucleic acid encoding an antigenic protein derived from *Sarcocystis neurona*, or a unique fragment thereof. In one embodiment, the invention provides novel isolated nucleic acids encoding membrane-associated polypeptides SnSAG2, SnSAG3, and SnSAG 4.

The present invention also provides purified antigenic polypeptide fragments encoded by the novel nucleic acid sequences set forth herein that encode for *Sarcocystis neurona*. In one embodiment, the invention provides purified antigenic proteins or purified antigenic polypeptide fragments encoded by the novel nucleic acid sequences set forth herein that encode for SnSAG2, SnSAG3, and SnSAG4. In another embodiment, the present invention provides a purified antigenic polypeptide fragment encoded by the nucleic acid sequences set forth herein or a selective portion thereof in a pharmaceutically acceptable carrier.

The present invention also provides isolated nucleic acids capable of selectively hybridizing with the nucleic acid from Sarcocystis neurona including, but not limited to, primers and probes for utilization in polymerase chain reaction (PCR) and other nucleic acid amplification techniques. The isolated nucleic acids of the present invention are capable of hybridizing under conditions of low, moderate, and high stringency with a nucleic acid from Sarcocystis neurona.

Further, the present invention provides vectors comprising the isolated nucleic acids, or degenerate variants thereof, set forth herein encoding Sarcocystis neurona or a unique fragment thereof and provides the vector in a host capable of expressing the polypeptide encoded by that nucleic acid.

Still yet further, the present invention also provides a purified polyclonal and or a monoclonal antibody specifically reactive with Sarcocystis neurona and a method of detection of Sarcocystis neurona utilizing the antibodies of the present invention.

The above-described embodiments provided by the present invention, provide a method for detecting Sarcocystis neurona in a biological sample, comprising detecting the presence in the sample of an antibody or fragment thereof which specifically binds to a polypeptide comprising an isolated amino acid sequence selected from the group set forth in the Sequence Listing as SEQ ID NO.: 24, SEQ ID NO: 26, and SEQ ID NO: 28. In one embodiment of the method, the biological sample is serum. In another embodiment, the present invention provides a method as described for detecting Sarcocystis neurona in cerebrospinal fluid (CSF).

Finally, the present invention provides a kit for detecting Sarcocystis neurona in a biological sample, comprising at least one isolated amino acid sequence selected from the group set forth in the Sequence Listing as SEQ ID NO.: 24, SEQ ID NO: 26, and SEQ ID NO: 28, and a reporter molecule for detecting a first antibody or fragment thereof which specifically binds to a polypeptide comprising the at least one isolated amino acid sequence. The reporter molecule may be any suitable detectable second antibody or fragment thereof which binds to the first antibody or fragment thereof, and which is labeled with a detectable moiety or bound to a substrate.

BRIEF DESCRIPTION OF THE DRAWINGS

FIG. 2 is a sequence comparison of mature SnSAG2 (SEQ ID NO.: 36) with TgSAG1 (SEQ ID NO.: 37) and TgSRS2 (SEQ ID NO.: 38). The sequences presented in the Figure are for the mature proteins after cleaving off the N-terminal signal peptide and the C-terminal signal for the GPI anchor. The S. neurona surface antigen SnSAG2 is most similar to the TgSAG1 family of T. gondii surface antigens. Similar to the other SnSAGs, SnSAG2 shares modest sequence identity to its TgSAG orthologues, but contains 6/6 conserved cysteine residues that have been observed in each half of the proto-typical two-domain apicomplexan SAG. SnSAG2 will also align with the carboxyl-terminal domain of the TgSAGs.

DETAILED DESCRIPTION OF THE INVENTION

Figure 1:
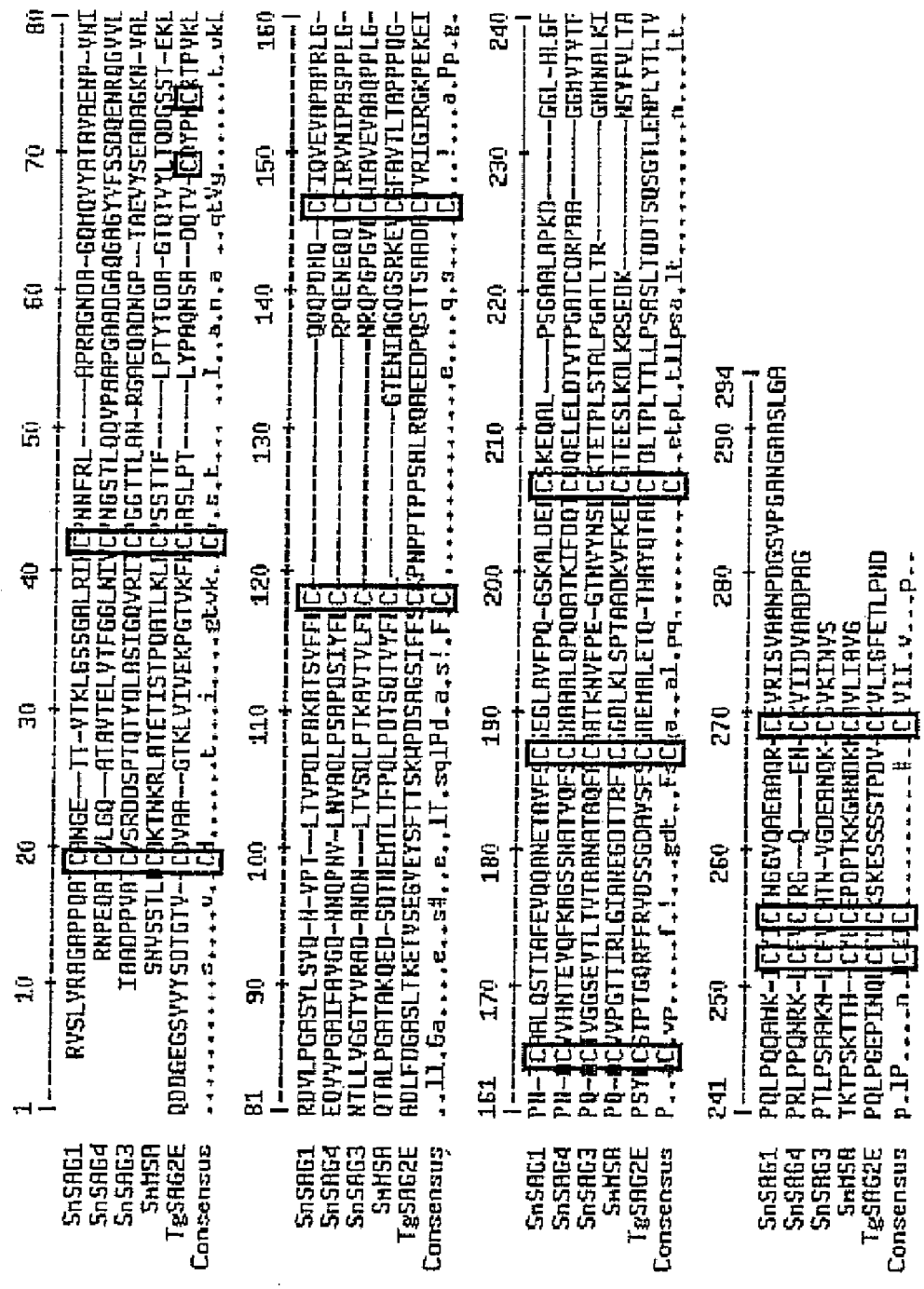
FIG. 1 is a sequence comparison of mature SnSAG1 (SEQ ID NO.:31), SnSAG4 (SEQ ID NO: 32), and SnSAG3 (SEQ ID NO.: 33) with SmMSA (SEQ ID NO.: 34) and TgSAG2E (SEQ ID NO.:35). The S. neurona surface antigens SnSAG1, SnSAG3 and SnSAG4 are most similar to the TgSAG2 family of T. gondi surface antigens. The sequences presented in the Figure are for the mature proteins after cleaving off the N-terminal signal peptide and the C-terminal signal for the GPI anchor. Sequence alignments of the predicted mature proteins revealed very moderate sequence identity (<25%). However, the SnSAGs contain 10/12 conserved cysteine residues that have been observed previously, suggesting that the SnSAGs have a tertiary structure that is similar to what has been determined for the TgSAGs/SRSs.

The present invention may be understood more readily by reference to the following detailed description of specific embodiments and the examples included therein. As used in the claims, "a" can mean one or more. As can be appreciated by one of skill in the art, methods and materials similar or equivalent to those described herein can be used in the practice of the present invention. All publications, patent applications, patents, and other references mentioned herein are incorporated by reference in their entirety in order to more fully describe the state of the art to which this invention pertains. It is noted that the abbreviated citations of literature referenced herein are set forth fully in U.S. patent application Ser. No. 10/369,430, the disclosure of which is also incorporated herein in its entirety by reference.

Although the present invention has been described with reference to specific details of certain embodiments thereof, it is not intended that such details should be regarded as limitations upon the scope of the invention except as and to the extent that they are included in the accompanying claims. In the case of a conflict with incorporated references, the present specification, including definitions, will control. In addition, the particular embodiments discussed below are illustrative only and not intended to be limiting.

The present invention satisfies the long felt need in the art by providing novel isolated nucleic acid sequences which encode antigenic proteins derived from *Sarcocystis neurona*, or which encode unique antigenic protein fragments thereof. As used herein, a "nucleic acid" means a chain of at least two or more nucleotides such as DNA (deoxyribonucleic acid) or RNA (ribonucleic acid). As used herein, a "purified" nucleic acid is one that is substantially separated from other nucleic acid sequences in a cell or organism in which the nucleic acid naturally occurs. Likewise, by "isolated" nucleic acid is meant separated from at least some of other nucleic acids found in the naturally-occurring organism. The nucleic acids of the present invention can include positive and negative strand RNA as well as DNA. The above terms encompass double-stranded DNA, single-stranded DNA, and RNA and are meant to include genomic and subgenomic nucleic acids found in the naturally-occurring *Sarcocystis neurona* organism. The nucleic acids contemplated by the present invention include a nucleic acid having sequences from which a *Sarcocystis neurona* cDNA can be transcribed; or allelic variants and/or homologs of thereof. By "capable of selectively hybridizing" is meant a sequence which does not hybridize with other nucleic acids to prevent an adequate positive hybridization with nucleic acids from *Sarcocystis neurona* and is meant to include stringent hybridization conditions including low, moderate and high stringency conditions. Such stringency conditions are known in the art, e.g., in US Patent Publication No.: 2002/0115828 A1. By "unique fragment" is meant a fragment of the nucleic acids set forth in the Sequence Listing that is less than the full length that can selectively hybridize with a RNA, DNA or cDNA sequence derived from the novel sequences set forth herein or that can selectively hybridize with nucleic acids from *Sarcocystis neurona*. Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective hybridization (Kunkel et al. Methods Enzmol. 1987: 154-367, 1987). As one of skill in the art can appreciate, there can be naturally occurring allelic variants and non-naturally occurring variants or modifications of the nucleic acids of the invention. For example, homologs or naturally occurring allelic variants of the nucleic acids of the invention having from about 50% and up to about 99% sequence identity are contemplated by the invention. Likewise, it is contemplated that non-naturally occurring variants or modifications of the nucleic acids of the invention can range from about 50% to about 99% sequence identity to native *S. neurona* are contemplated.

In particular, one embodiment of the present invention provides isolated nucleic acids derived from three *Sarcocystis neurona* cluster sequences, namely Sn Cluster 144, Sn Cluster 21 and Sn Cluster 4, which comprise the nucleotide sequences set forth in the Sequence Listing as SEQ ID NOS: 1, 3, and 29 respectively and the sequences complimentary thereto. Also provided by the invention are the corresponding protein or polypeptide amino acid sequences for these three *Sarcocystis neurona* cluster sequences. The polypeptide sequence comprising Sn Cluster 144 is set forth in the Sequence Listing as SEQ ID NO: 2. The polypeptide sequence comprising Sn Cluster 21 is set forth in the Sequence Listing as SEQ ID NO: 4 and the polypeptide sequence comprising Sn Cluster 4 is set forth in the Sequence Listing as SEQ ID NO: 30. As used herein, the terms "polypeptide" and "protein" are used interchangeably and are meant to include any peptide-linked chain of amino acids, regardless of length or post-translational modification, e.g., glycosylation or phosphorylation. By "purified" polypeptide is meant a polypeptide that has been substantially separated or isolated away from other polypeptides in a cell, organism, or mixture in which the polypeptide occurs.

Similar to other members of the Apicomplexa, *S. neurona* is an obligate intracellular pathogen that utilizes a number of unique structures and molecules (i.e., virulence factors) to support its parasitic lifestyle. Parasite surface molecules are virulence factors that are typically novel and undoubtedly important since they are responsible for the initial interactions with the host cell surface and host immune response. In *Toxoplasma gondii*, for example, an extensive family of 25+ surface antigens has been identified, which are developmentally regulated and exhibit various levels of sequence similarity to either of the major *T. gondii* surface antigens TgSAG1 or TgSAG2. These surface molecules appear to be involved in receptor/ligand interactions with the host cell surface, and there is increasing evidence that some of the *T. gondii* SAGs are involved in modulation of host immune responses.

Figure 4:
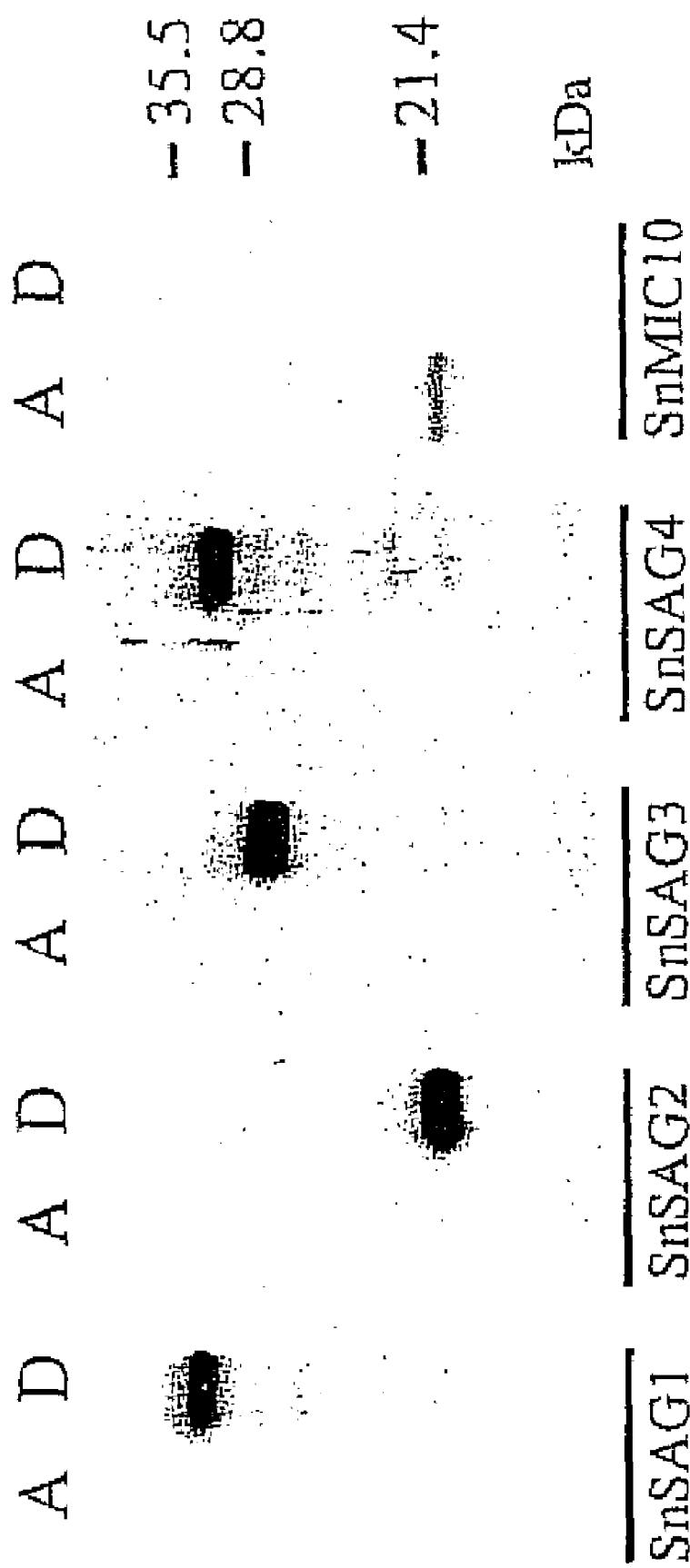
FIG. 4 shows the SnSAGs are membrane-associated in Sarcocystis neurona merozites. Triton X-114 partitioning assays indicated that the SnSAGs are associated with membranes, consistent with their surface localization via glycolipid anchoring. Western blot analysis of the partitioned proteins with the SnSAG-specific polyclonal antisera revealed that all four SnSAGs were separated exclusively into the detergent phase (D). The control protein, SnMIC10, was partitioned into the aqueous phase (A), as expected.
Figure 5:
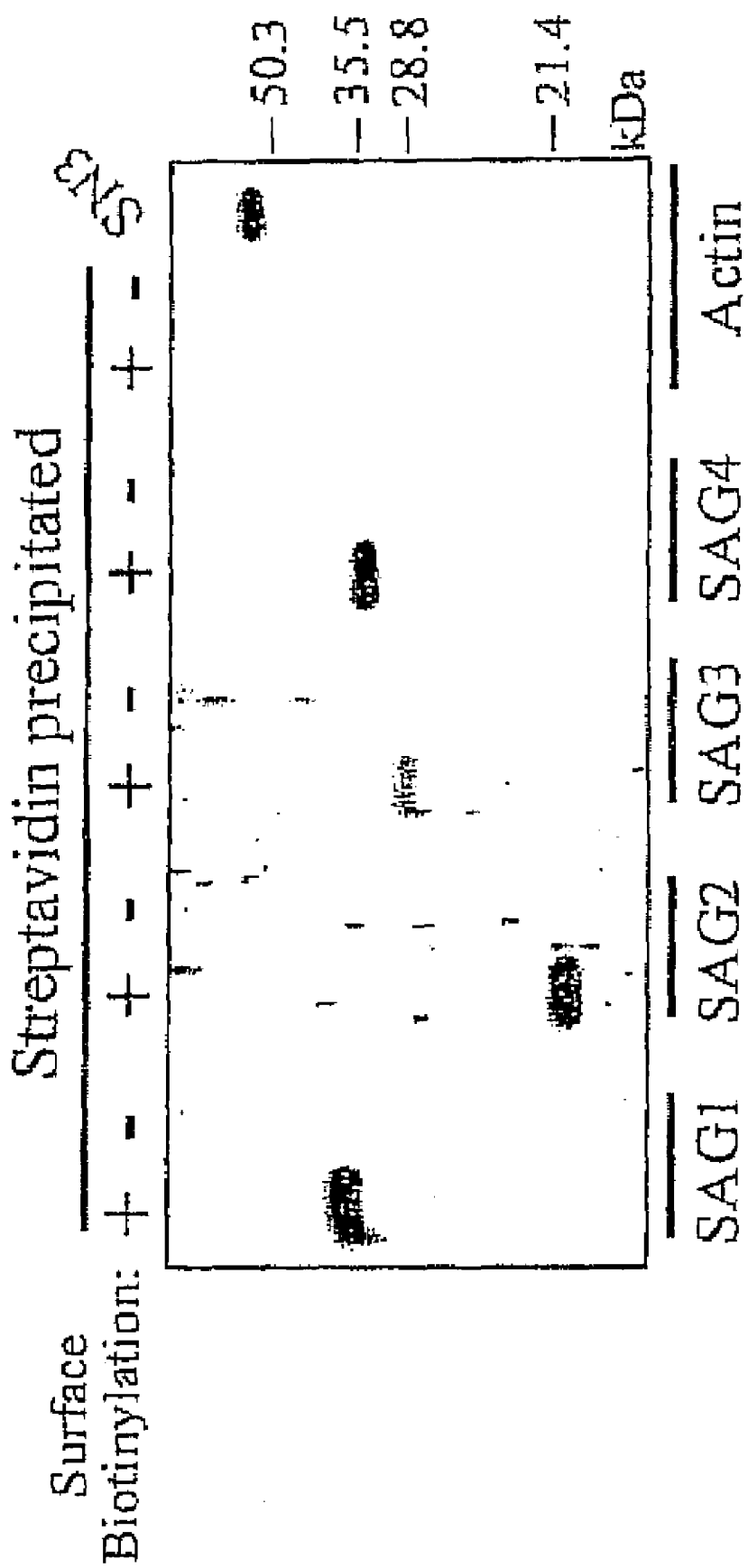
FIG. 5 shows that the four SnSAGs are displayed on the surface of Sarcocystis neurona merozoites. Surface biotinylation of S. neurona merozoites indicated that the four SnSAGs are displayed on the surface of the parasite. Western blot analysis with the SnSAG-specific antisera revealed each of the SnSAGs in the biotinylated protein fraction precipitated with immobilized streptavidin. The SnSAGs were not present in the non-labeled parasites, thus indicating that the streptavidin precipitation were specific for biotin-labeled proteins. The negative control protein (actin) was not detected in the biotin-labeled/streptavidin-precipitated protein fraction.

In one embodiment, the present invention provides identity and characterization of certain of the virulence factors of *S. neurona*. In particular, the present invention provides four isolated nucleic acids of *S. neurona* (genes) that encode parasitic surface antigens. A sequencing project was conducted that generated approximately 8500 expressed sequence tags (ESTs) from this organism. Examination of this sequence database has revealed a family of at least four *S. neurona* surface antigens that are orthologues of the SAG/SRS family of surface proteins in *T. gondii*. Each protein is predicted to contain an amino-terminal signal peptide and a carboxyl-terminal glycolipid anchor addition site, indicating surface localization, and Triton X-114 partitioning and surface biotinylation assays confirmed that all four proteins are membrane-associated and displayed on the *S. neurona* merozoite surface (See, FIGS. 4 and 5). Additionally, these novel *S. neurona* proteins possess multiple conserved cysteine residues that have been described previously for *T. gondii* SAGs and which are likely important for the tertiary structure of the proteins (See, FIGS. 1 and 2). Due to their surface localization and relative homology to *T. gondii* surface antigens, these *S. neurona* proteins have been designated SnSAG1, SnSAG2, SnSAG3, and SnSAG4.

Accordingly, one embodiment of the present invention comprises an isolated nucleic acid as set forth in the Sequence listing as SEQ ID NO: 21. The nucleic acid identified in SEQ ID NO: 21 comprises an 828-nucleotide open reading frame of the SnSAG1 gene of *Sarcocystis neurona* which encodes a 276 amino acid polypeptide set forth in the Sequence Listing as SEQ ID NO: 22. The polypeptide encoded by SEQ ID NO: 22 has a predicted amino-terminal signal peptide (indicating expression via the secretory pathway) and a glycolipid anchor addition site at the carboxy-terminal end (indicating surface localization). Database searches with the predicted protein sequence of SnSAG1 (rSnSAG1) revealed significant similarity (alignment score=80, E value=2×10−14) to a 31 kDa surface antigen from *Sarcocystis muris*.

Figure 3:
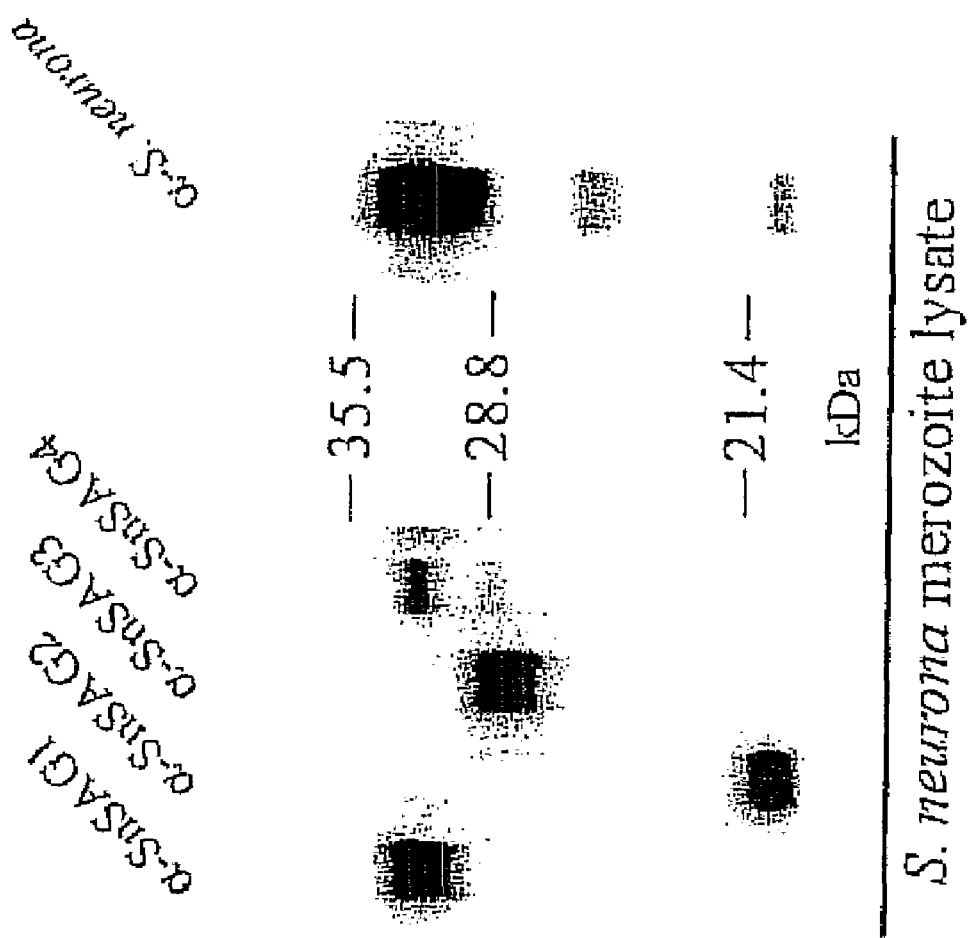
FIG. 3 shows a Western blot analysis of the SnSAGs in S. neurona merozoites. The SnSAG genes were expressed in E. coli, and monospecific polyclonal antisera were generated against the recombinant proteins. Western blot analysis of reduced antigen revealed that each SnSAG migrated significantly higher than its predicted molecular weight, consistent with what has been observed for the T. gondii SAGs/SRS. SnSAG1 and SnSAG4 co-migrated and corresponded to the immunodominant band at about 30-32 kDa. SnSAG2 corresponded to an immunodominant band at approximately 18-20 kDa.

A recombinant form of the *Sarcocystis neurona* SnSAG1 (rSnSAG1) has been expressed in *E. coli*. Western blot analysis of rSnSAG1 demonstrated that the recombinant antigen is recognized by antiserum from a rabbit that was immunized with *S. neurona* merozoites and by antibodies in cerebrospinal fluid (CSF) from an EPM (*Sarcocystis neurona* infected) horse (See, e.g., FIG. 3).

Another embodiment of the present invention comprises an isolated nucleic acid as set forth in the Sequence listing as SEQ ID NO: 23. The nucleic acid identified in SEQ ID NO: 23 comprises an 975 nucleotide open reading frame of the SnSAG2 gene of *Sarcocystis neurona* which encodes a 168 amino acid polypeptide set forth in the Sequence Listing as SEQ ID NO: 24.

The present invention also provides an isolated nucleic acid as set forth in the Sequence listing as SEQ ID NO: 25. The nucleic acid identified in SEQ ID NO: 25 comprises an 1585 nucleotide open reading frame of the SnSAG3 gene of *Sarcocystis neurona* which encodes a 281 amino acid polypeptide set forth in the Sequence Listing as SEQ ID NO: 26.

Also provided by the present invention is an isolated nucleic acid as set forth in the Sequence listing as SEQ ID NO: 27. The nucleic acid identified in SEQ ID NO: 27 comprises an 1111 nucleotide open reading frame of the SnSAG4 gene of *Sarcocystis neurona* which encodes a 287 amino acid polypeptide set forth in the Sequence Listing as SEQ ID NO: 28.

As set forth more fully below, these genes have been expressed as recombinant proteins in *E. coli*. The recombinant SnSAG proteins can be implemented into antibody-capture ELISAs and used to detect the presence of *S. neurona* antibodies in a sample. Likewise, the recombinant proteins provided by the invention can be used as reagents for use in vaccines against *S. neurona*.

Another embodiment of the present invention includes the discovery of additional novel expressed sequence tags (EST) that encode novel antigenic peptides for utilization in the vaccines and diagnostic kits as disclosed by this invention.

In particular, cluster analysis of the *Sarcocystis neurona* expressed sequence tags (ESTs) generated from the cSn.1 cDNA library has revealed a gene family that encodes at least eight homologous proteins. Of the approximately 8500 *S. neurona* ESTs that have been generated thus far, roughly 540 sequences can be placed in this gene family, which has been provisionally designated SnGF1 (*S. neurona* Gene Family 1). Based on its relative abundance in the collection of *S. neurona* ESTs, SnGF1 encodes a set of similar proteins (at least eight) that are highly expressed and most likely play significant roles in the biology of *S. neurona* (i.e., parasite virulence factors). In addition to their biological importance, the abundance of these proteins would suggest that they elicit significant immune responses in infected animals. Collectively, the characteristics of the novel nucleic acids of SnGF1, and the encoded proteins therefrom, make this gene family well suited for the development of improved diagnostics and/or vaccines for EPM as set forth herein.

The eight SnGF1 isoforms identified thus far have been designated SnGF1a-h. These genes are predicted to encode proteins of, e.g., 109 amino acids, 106 amino acids, and 107 amino acids in length, and the proteins share approximately 70% to 80% sequence identity. These proteins have a predicted N-terminal signal peptide and a predicted transmembrane domain near the C-terminus. The SnGF1 members show no similarity to sequences in the current public gene databases, suggesting that SnGF1 is relatively unique to *S. neurona*.

Accordingly, one embodiment of the present invention provides an isolated nucleic acid designated SnGF1a which comprises the nucleic acid set fort in SEQ ID NO: 5 and sequences complimentary thereto. Another embodiment of the invention comprises the polypeptide sequence encoded by SnGF1a set forth in the Sequence Listing as SEQ ID NO: 6.

Another embodiment of the present invention provides an isolated nucleic acid designated SnGF1b which comprises the nucleic acid set forth in SEQ ID NO: 7 and sequences complimentary thereto. Another embodiment of the invention comprises the polypeptide sequence encoded by SnGF1b set forth in the Sequence Listing as SEQ ID NO: 8.

Yet another embodiment of the present invention provides an isolated nucleic acid designated SnGF1c which comprises the nucleic acid set forth in SEQ ID NO: 9 and sequences complimentary thereto. Another embodiment of the invention comprises the polypeptide sequence encoded by SnGF1c set forth in the Sequence Listing as SEQ ID NO: 10.

Still another embodiment of the present invention provides an isolated nucleic acid designated SnGF1d which comprises the nucleic acid set forth in SEQ ID NO: 11 and sequences complimentary thereto. Another embodiment of the invention comprises the polypeptide sequence encoded by SnGF1d set fort in the Sequence Listing as SEQ ID NO: 12.

The present invention also provides an isolated nucleic acid designated SnGF1e which comprises the nucleic acid set fort in SEQ ID NO: 13 and sequences complimentary thereto. Another embodiment of the invention comprises the polypeptide sequence encoded by SnGF1e set forth in the Sequence Listing as SEQ ID NO: 14.

Another embodiment of the present invention provides an isolated nucleic acid designated SnGF1f which comprises the nucleic acid set forth in SEQ ID NO: 15 and sequences complimentary thereto. Another embodiment of the invention comprises the polypeptide sequence encoded by SnGF1f set forth in the Sequence Listing as SEQ ID NO: 16.

Yet another embodiment of the present invention provides an isolated nucleic acid designated SnGF1g which comprises the nucleic acid set forth in SEQ ID NO: 17 and sequences complimentary thereto. Another embodiment of the invention comprises the polypeptide sequence encoded by SnGF1g set forth in the Sequence Listing as SEQ ID NO: 18.

Still another embodiment of the present invention provides an isolated nucleic acid designated SnGF1h which comprises the nucleic acid set forth in SEQ ID NO: 19 and sequences complimentary thereto. Another embodiment of the invention comprises the polypeptide sequence encoded by SnGF1h set forth in the Sequence Listing as SEQ ID NO: 20.

The present invention provides isolated nucleic acids as set forth in the Sequence Listing and nucleic acid reagents derived therefrom which can be utilized to diagnose and prevent infection of *S. neurona*. Purified polypeptides encoded by the nucleic acids are also provided. These polypeptides can be utilized in methods of diagnosis or as vaccine components for prevention of infection. Vectors are also provided which comprise the nucleic acids of the present invention. The vectors can be utilized in host expression systems to produce antigenic peptide reagents for diagnostic and prophylactic applications. The present invention also provides purified antibodies selectively reactive with *S. neurona*. These antibodies can be used in various diagnostic methods or as a therapeutic.

In one embodiment, the invention provides purified antigenic polypeptides encoded by the nucleic acids set forth in the Sequence Listing. The invention also provides these antigenic polypeptides in a pharmaceutically acceptable carrier. The amino acid sequence of these polypeptides can be deduced from the nucleotide sequences set forth in the Sequence Listing.

Purified antigenic polypeptide fragments encoded by the nucleic acids of the present invention are also contemplated. As used herein, "purified" means the antigen is at least sufficiently free of contaminants or cell components with which the antigen normally occurs to distinguish the antigen from the contaminants or components. Purified antigenic polypeptides of *S. neurona* and antigenic fragments thereof of the present invention are also referred to herein as "the antigen" or "the *S. neurona* antigen." It is contemplated that the antigenic fragments can be encoded from any portion of the nucleic acid encoding *S. neurona* as set forth in the Sequence Listing, but especially from fragments encoded by the open reading frames set forth in SEQ ID NOS: 24, 26 and 28 as described herein. Specifically, one example provides an approximately 12 kDa antigenic polypeptide encoded by an open reading frame of SEQ ID NO: 24 consisting essentially of the amino acids encoded by the nucleotide as sequence set forth in the Sequence Listing as SEQ ID NO: 23.

An antigenic fragment of the antigen can be isolated from the whole antigen by chemical or mechanical disruption. The purified fragments thus obtained can be tested to determine their antigenicity and specificity by the methods taught herein. Antigenic fragments of the antigen can also be synthesized directly. An immunoreactive fragment is generally an amino acid sequence of at least about five consecutive amino acids derived from the antigen amino acid sequence.

The polypeptide fragments of the present invention can also be recombinant proteins obtained by cloning nucleic acids encoding the polypeptide in an expression system capable of producing the antigenic polypeptide or fragments thereof.

Once the amino acid sequence of the antigen is provided, it is also possible to synthesize, using standard peptide synthesis techniques, peptide fragments chosen to be homologous to immunoreactive regions of the antigen and to modify these fragments by inclusion, deletion or modification of particular amino acids residues in the derived sequences. Thus, synthesis or purification of an extremely large number of peptides derived from the antigen is possible.

The amino acid sequences of the present polypeptides can contain an immunoreactive portion of the *S. neurona* antigen attached to sequences designed to provide for some additional property, such as solubility. The amino acid sequences of an *S. neurona* antigen can include sequences in which one or more amino acids have been substituted with another amino acid to provide for some additional property, such as to remove/add amino acids capable of disulfide bonding, to increase its bio-longevity, alter enzymatic activity, or alter interactions, e.g., with gastric acidity. In any case, the peptide should posses a bioactive property, such as immunoreactivity, immunogenicity, etc.

The purified polypeptide fragments thus obtained can be tested to determine their immunogenicity and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a horse or a guinea pig, the condition of the subject, the size of the subject, etc. Thereafter an animal so inoculated with the antigen can be exposed to the parasite to test the potential vaccine effect of the specific immunogenic fragment. The specificity of a putative immunogenic fragment can be ascertained by testing sera, other fluids or lymphocytes from the inoculated animal for cross reactivity with other closely related *Sarcocystis* spp.

A vector comprising the nucleic acids of the present invention is also provided. The vectors of the invention can be in a host capable of expressing the antigenic polypeptide fragments contemplated by the present invention. There are numerous *E. coli* expression vectors known to one of ordinary skill in the art useful for the expression of the antigen. Other microbial hosts suitable for use include bacilli, such as *Bacillus subtilis*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters can be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, for example, an amino terminal methionine can be provided by insertion of a Met codon 5' and in-frame with the antigen. Also, the carboxyterminal extension of the antigenic fragments can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. In one example, the *Saccharomyces cerevisiae* pre-pro-alpha-factor leader region (encoded by the MF.alpha.-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or .beta.-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of a cDNA or opposite strand RNA corresponding to the antigen coding sequence can be confirmed by northern analysis. A number of other suitable host cell lines capable of secreting intact proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells can be employed, similar to those developed for the expression of human gammainterferon, tissue plasminogen activator, clotting Factor VIII, hepatitis B virus surface antigen, protease NexinI, and eosinophil major basic protein. Further, the vector can include CMV promoter sequences and a polyadenylation signal available for expression of inserted nucleic acid in mammalian cells (such as COS7).

The nucleic acid sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

One presently preferred vector system for expression of the peptides of the invention comprises the use of Alphavirus vector constructs, for example, as set forth in U.S. Pat. Nos. 5,643,576; 5,843,723; 6,156,558; and 6,242,259, the teachings of which are hereby incorporated herein by reference.

A purified monoclonal antibody specifically reactive with S. neurona is also provided. The antibodies can be specifically reactive with a unique epitope of the antigen or they can also react with epitopes of other organisms. The term "reactive" means capable of binding or otherwise associating non randomly with an antigen. "Specifically reactive" as used herein refers to an antibody or other ligand that does not cross react substantially with any antigen other than the one specified, in this case, S. neurona. Antibodies can be made as described in the Examples (see also, Harlow and Lane, Antibodies; A Laboratory Manual, Cold Spring Harbor Laboratory, Cold Spring Harbor, N.Y., 1988). Briefly purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen clone libraries for cells secreting the antigen. Those positive clones can then be sequenced (see, for example, Kelly et al., Bio/Technology, 10: 163-167, (1992) and Bebbington et al., Bio/Technology, 10: 169-175, (1992).

The antibody can be bound to a substrate or labeled with a detectable moiety or both bound and labeled. The detectable moieties contemplated by the present invention include, but are not limited to fluorescent, enzymatic and radioactive markers.

A purified S. neurona antigen bound to a substrate and a ligand specifically reactive with the antigen are also contemplated. Such a purified ligand specifically reactive with the antigen can be an antibody. The antibody can be a monoclonal antibody obtained by standard methods and as described herein. The monoclonal antibody can be secreted by a hybridoma cell line specifically produced for that purpose (Harlow and Lane, 1988). Likewise, nonhuman polyclonal antibodies specifically reactive with the antigen are within the scope of the present invention. The polyclonal antibody can also be obtained by the standard immunization and purification protocols (Harlow and Lane, 1988).

The present invention provides a method of detecting the presence of S. neurona in a subject, comprising the steps of contacting an antibody-containing sample from the subject with a detectable amount of the antigenic polypeptide fragment of the present invention and detecting the reaction of the fragment and the antibody, the reaction indicating the presence of the S. neurona or a previous infection with S. neurona.

One example of the method of detecting S. neurona is performed by contacting a fluid or tissue sample from the subject with an amount of a purified antibody specifically reactive with the antigen as defined herein, and detecting the reaction of the ligand with the antigen. It is contemplated that the antigen will be on intact cells containing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, cerebrospinal fluid, saliva, feces and urine. Other possible examples of body fluids include sputum, mucus, gastric juice and the like.

Enzyme immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Another immunologic technique that can be useful in the detection of S. neurona or previous S. neurona infection utilizes monoclonal antibodies (MAbs) for detection of antibodies specifically reactive with S. neurona antigen. Briefly, sera or other body fluids from the subject is reacted with the antigen bound to a substrate (e.g. an ELISA 96-well plate). Excess sera is thoroughly washed away. A labeled (enzyme-led, fluorescent, radioactive, etc.) monoclonal antibody is then reacted with the previously reacted antigen serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

A micro-agglutination test can also be used to detect the presence of S. neurona in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or capable of being detected by a spectrophotometer. In a modification of the above test, antibodies specifically reactive with the antigen can be bound to the beads and antigen in the tissue or body fluid thereby detected.

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides S. neurona antigen for the detection of infectious, S. neurona or previous S. neurona infection other serological methods such as flow cytometry and immunoprecipitation can also be used as detection methods.

In the diagnostic methods taught herein, the antigen can be bound to a substrate and contacted by a fluid sample such as serum, cerebrospinal fluid, urine, saliva, feces or gastric juice. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecifically with, the ligand or reacted antibody, will be selected for its ability to react with multiple sites on the primary antibody. Thus, for example, several molecules of the secondary antibody can react with each primary antibody, making the primary antibody more detectable.

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, 1988).

The antigen, e.g., a purified antigenic polypeptide fragment encoded by the Sequence Listing of this invention can be used in the construction of a vaccine comprising an immunogenic mount of the antigen and a pharmaceutically acceptable carrier. The vaccine can be the entire antigen, the antigen on an intact S. neurona organism, E. coli or other strain, or an epitope specific to the antigen. The vaccine can also be potentially cross-reactive with antibodies to other antigens. The vaccine can then be used in a method of preventing EPM or other complications of S. neurona infection.

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

The pharmaceutically acceptable carrier can comprise saline or other suitable carriers (Arnon, R. (Ed.) Synthetic Vaccines I: 83-92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.). 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention provides methods of preventing or treating S. neurona infection and the associated diseases by administering the vaccine to a subject.

Nucleic acid vaccines against S. neurona are also contemplated by the invention. The antigenic agent for use in the vaccines of the invention can be any nucleic acid, e.g., as set forth in the Sequence Listing, that can stimulate an immune response against, e.g., SnSAG2, SnSAG3 or SnSAG4 when administered to a subject. Suitable nucleic acids include those that encode the native proteins of S. neurona, e.g., SnSAG2, SnSAG3 or SnSAG4 protein or a variant or antigenic peptide fragment thereof, such as, e.g., the nucleic acid set forth in the Sequence listing as SEQ ID NO:23, SEQ ID NO:25 or SEQ ID NO:27. The nucleic acid used as a vaccine can be e.g., a naked DNA, or the nucleic acid can be incorporated in an expression vector as set forth herein, e.g., in an Alpha virus vector (see, e.g., Rosenberg, S. A., Immunity 10:281, 1999).

The presence of S. neurona can also be determined by detecting the presence of a nucleic acid specific for S. neurona or the antigens of S. neurona encoded by the nucleic acids set forth herein. The present invention provides a method of detecting the presence of S. neurona in a subject, comprising detecting the presence of the nucleic acid encoding an S. neurona antigen. As set forth more fully in the examples below, the specificity of these sequences for S. neurona can be determined by conducting a computerized comparison with known sequences, catalogued in GenBank, a computerized database, using the computer programs Word Search or FASTA of the Genetics Computer Group (Madison, Wis.), which search the catalogued nucleotide sequences for similarities to the nucleic acid in question.

The nucleic acid specific for S. neurona antigen can be detected utilizing a nucleic acid amplification technique, such as polymerase chain reaction or ligase chain reaction. Alternatively, the nucleic acid is detected utilizing direct hybridization or by utilizing a restriction fragment length polymorphism. For example, the present invention provides a method of detecting the presence of S. neurona comprising ascertaining the presence of a nucleotide sequence associated with a restriction endonuclease cleavage site. In addition, PCR primers which hybridize only with nucleic acids specific for S. neurona can be utilized. The presence of amplification indicates the presence of S. neurona sequence. In another embodiment a restriction fragment of a nucleic acid sample can be sequenced directly using, techniques known in the art and described herein and compared to the known unique sequence to detect S. neurona. In a further embodiment, the present invention provides a method of detecting the presence of S. neurona by selective amplification by the methods described herein. In yet another embodiment S. neurona can be detected by directly hybridizing the unique sequence with a S. neurona selective nucleic acid probe. Furthermore, the nucleotide sequence could be amplified prior to hybridization by the methods described above.

Alternative probing techniques, such as ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is fall complementarity. If a mismatch is present there is significantly reduced hybridization.

The polymerase chain reaction (PCR) and reverse transcriptase PCR are techniques that amplify specific nucleic acid sequences with remarkable efficiency. Repeated cycles of denaturation, primer annealing and extension carried out with polymerase; e.g., a heat stable enzyme Taq polymerase, leads to exponential increases in the concentration of desired nucleic acid sequences. Given a knowledge of the nucleotide sequence of S. neurona as set forth herein, synthetic oligonucleotides can be prepared which are complementary to sequences which flank the nucleic acid of interest. Each oligonucleotide is complementary to one of the two strands. The nucleic acid can be denatured at high temperatures (e.g., 95.degree. C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template. The end product is then denatured again for another cycle. After this three-step cycle has been repeated several times, amplification of a nucleic acid segment by more than one million-fold can be achieved. The resulting nucleic acid may then be directly sequenced.

In yet another method, PCR may be followed by restriction endonuclease digestion with subsequent analysis of the resultant products. Nucleotide substitutions can result in the gain or loss of specific restriction endonuclease sites. The gain or loss of a restriction endonuclease recognition site facilitates the detection of the organism using restriction fragment length polymorphism (RFLP) analysis or by detection of the presence or absence of a polymorphic restriction endonuclease site in a PCR product that spans the sequence of interest.

For RFLP analysis, nucleic acid is obtained, for example from the blood, cerebrospinal fluid, gastric specimen, saliva, dental plaque, other bodily fluids of the subject suspected of containing *S. neurona*, is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, *S. neurona* nucleic acid is detected and their mobility on the gel by determining the number of bands detected and comparing this pattern to the nucleic acid from *S. neurona*.

Similar creation of additional restriction sites by nucleotide substitutions at the disclosed mutation sites can be readily calculated by reference to the genetic code and a list of nucleotide sequences recognized by restriction endonucleases. Single strand conformational analysis (SSCA) offers a relatively quick method of detecting sequence changes which may be appropriate in at least some instances.

In general, primers for PCR and LCR are usually about 20 bp in length and the preferable range is from 15-25 bp. Better amplification is obtained when both primers are the same length and with roughly the same nucleotide composition. Denaturation of strands usually takes place at about 94.degree. C. and extension from the primers is usually at about 72.degree. C. The annealing temperature varies according to the sequence under investigation. Examples of reaction times are: 20 mins denaturing; 35 cycles of 2 min, 1 min, 1 min for annealing, extension and denaturation; and finally a 5 min extension step.

PCR amplification of specific alleles (PASA) is a rapid method of detecting single-base mutations or polymorphisms. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on *S. neurona* isolates or samples obtained from an individual, it can serve as a method of detecting the presence of *S. neurona*. As mentioned above, a method known as ligase chain reaction (LCR) can be used to successfully detect a single-base substitution. LCR probes may be combined or multiplexed for simultaneously screening for multiple different mutations. Thus, LCR can be particularly useful where, as here, multiple mutations are predictive of the same disease.

The present invention is more particularly described in the following examples which are intended as illustrative only, since numerous modifications and variations therein will be apparent to those skilled in the art.

EXAMPLES

Identification and Characterization of SnSAG1

Surface biotinylation of extracellular merozoites revealed only two dominant labeled molecules that migrate at about 30 kDa and 16 kDa in SDS-PAGE. Analysis of a *S. neurona* EST database (currently 1800+ sequences) identified an orthologue of the 31-kDa surface antigen from *Sarcocystis muris*. The sequence of the *S. neurona* surface antigen gene, designated SnSAG1, is predicted to encode a 276-residue protein with an amino-terminal signal peptide and a carboxy-terminal GPI anchor addition. Antiserum raised against recombinant SnSAG1 recognized a 25-kDa antigen in western blots of non-reduced *S. neurona* lysates, consistent with the molecular weight predicted for the mature SnSAG1. Under reducing conditions, SnSAG1 migrated aberrantly at about 30 kDa, similar to what has been observed in western blot analyses of reduced *T. gondii* surface antigens. Immunofluorescence labeling of SnSAG1 during intracellular growth of *S. neurona* indicated that the protein is expressed throughout schizogony. Interestingly, a filamentous staining pattern was observed in intermediate schizonts that likely reflects localization of the surface antigen to previously-described invaginations of the schizont surface membrane.

Parasite Culture

*S. neurona* strain SN3 [Granstrom, 1992 #1600] merozoites were propagated by serial passage in bovine turbinate (BT) cells and maintained in RPMI 1640 medium supplemented with 10% fetal bovine serum, 2 mM sodium pyruvate, Pen/Strep Fungizone (BioWittaker, Inc.). Extracellular merozoites were harvested and purified from disrupted host cell monolayers by filtration through 3.0 μm membranes, as described previously for *Neospora caninium* [Howe, 1997 #1372].

Immunoscreen of *S. neurona* cDNA Library

Construction and analyses of the cSn.1 *S. neurona* merozoite cDNA library has been described previously [Howe, 2001 #1787]. The library was plaqued for 3 hrs at 42° C. on XL1-Blue MRF' *E. coli* host cells (Stratagene) grown on 150 mm NZY agar plates. When plaques became visible, plates were overlayed with nitrocellulose filters previously soaked in 10 mM isopropyl-β-D-thiogalactopyranoside (IPTG) for an additional 3 hr incubation at 37° C. Filters were lifted from the plates, washed with TNT buffer (10 mM Tris-HCl, pH 7.5, 150 mM NaCl, 0.05% Tween 20), and blocked in phosphate buffered saline (PBS), 5% dry milk, 5% normal goat serum, 0.05% Tween 20.

Antigenic cDNA clones were identified by screening with cerebrospinal fluid (CSF) from a horse that had been naturally infected with *S. neurona* and exhibited a high titer of intrathecal antibodies against *S. neurona* in western blot analysis. Prior to screening the *S. neurona* cDNA library, the CSF was diluted 1:20 in PBS, 0.1% dry milk, 0.1% normal goat serum, 0.05% Tween 20 and incubated for 30 min with filters carrying plaque lifts of a previously-described *N. caninum* cDNA library [Howe, 1999 #1759] to remove antibodies that were reactive with *E. coli* and phage proteins. After Results Isolation and Analysis of Immunoreactive cDNA Clones A primary screen of the cSn.1 cDNA library identified multiple immunoreactive phage plaques, and a total of 25 plaques were isolated and resuspended in SM buffer. Amplification of the cDNA inserts with T3 and T7 oligonucleotides revealed that 22 of the phage clones had similar lengths of approximately 1500 base pairs (bp), and sequence analysis using T3 primer indicated that these 22 cDNAs represent the same gene. A secondary screen was performed on five of the selected cDNAs, and two highly reactive phage clones, designated SnAgI.8 and SnAgI.9, were chosen for further analyses.

To obtain a preliminary identification of the parasite protein encoded by the selected cDNAs, the SnAgI.9 clone was used to affinity purify antibodies that bind the antigen expressed by this clone, and the eluted antibodies were used to probe a western blot of S. neurona merozoite lysate. As shown in FIG. 1, the purified antibodies reacted with an approximately 31-kDa antigen in reduced S. neurona lysate. Furthermore, the antigen revealed by the phage-purified antibodies comigrated with a protein that is recognized by equine or rabbit antisera against S. neurona as the major immunodominant antigen of this parasite (FIG. 1, lanes 2 and 3). This result implies that the 22 matching cDNA clones isolated during the library screen and represented by SnAgI.8 and SnAgI.9 encode the immunodominant antigen of S. neurona.

Full-length sequence analysis of SnAgI.8 revealed a cDNA insert of 1493 nucleotides, with an open reading frame (ORF) that encodes a 276 amino acid protein. Sequence analysis of SnAgI.9 indicated that this clone was virtually identical to SnAgI.8, although its 3' untranslated region (UTR) was approximately 160 nucleotides longer due to an alternative polyadenylation site. A hydrophobicity plot of the encoded protein showed hydrophobic domains at both termini, which correspond to a predicted signal peptide at the amino terminus and a GPI anchor addition sequence at the carboxyl terminus (data not shown). The signal peptide cleavage is predicted to occur at $Ala^{15}$-$Arg^{16}$ (SignalP; [Nielsen, 1997 #2047], and the most likely GPI transamidase cleavage site is predicted to be at $Ala^{247}$-$Asn^{248}$ (DGPI; Swiss Institute of Bioinformatics). A single N-glycosylation site was predicted at residues 140-143. Removal of the N-terminal and C-terminal signal sequences results in a mature protein of 242 amino acids that has a predicted molecular weight of 24.2 kDa before any potential post-translational modifications (e.g., glycolipid anchor addition, glycosylation).

Figure 2:
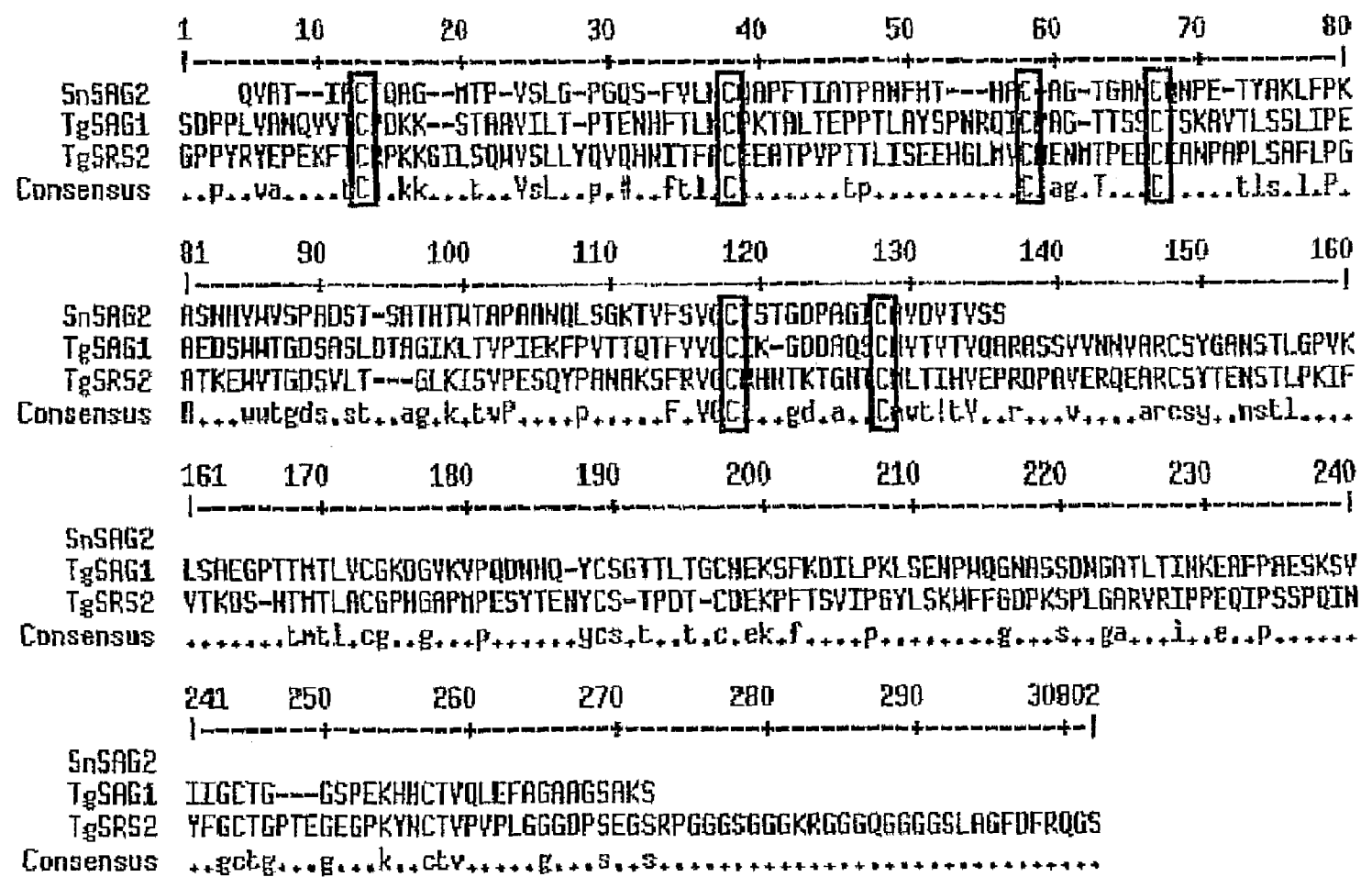

To identify homology to previously characterized sequences, BLAST searches [Altschul, 1990 #616] of the non-redundant GenBank databases were conducted with the SnAgI.8 coding sequence as the query. These searches revealed a statistically significant similarity to the 31 kDa major surface antigen of Sarcocystis muris [Eschenbacher, 1992 #1767] and a less significant but recognizable similarity to several SAG2-related surface antigens from T. gondii [Lekutis, 2000 #2049]. (FIG. 2). In conjunction with the western blot analysis and the predictions of a signal peptide and a GPI-anchor addition, these results suggested that the gene represented by the SnAgI.8 and SnAgI.9 cDNAs encodes an immunodominant surface antigen of S. neurona; consequently, we tentatively designated this protein SnSAG1, following the genetic nomenclature that is utilized for the related apicomplexan parasites T. gondii and N. caninum [Sibley, 1991 #13; Howe, 1999 #1759].

The sequence analysis for SnSAG2, SnSAG3, and SnSAG4 as well as for the SnGF Cluster sequences provided by the invention and set forth herein have been derived in a fashion similar to that set forth above for SnSAG1. These novel nucleotide sequences and protein sequences of Sarcocystis neurona can be utilized in the production of vaccines and/or antigen/antibody kits for prevention and diagnosis of Sarcocystis neurona infection. One preferred embodiment of the invention is a vaccine comprised of an alpha virus expression vector and nucleic acid selected from the nucleic acid sequences disclosed herein.

Identification of S. neurona Surface Antigens and Expression as Recombinant Proteins Analysis of the S. neurona EST database revealed four paralogous proteins that are homologous to the SAG and SRS surface antigens of Toxoplasma gondii. Each S. neurona gene was predicted to encode a protein that possessed an amino-terminal signal peptide and a carboxyl-terminal glycolipid anchor site, consistent with the proteins being surface antigens. Because of their similarity to Toxoplasma SAGs and their probable surface display on merozoites, the four S. neurona proteins were designated SnSAG1, SnSAG2, SnSAG3, and SnSAG4. The four putative surface antigens were each expressed as a recombinant protein in E. coli, and these were used to immunize rabbits and rats for monospecific polyclonal antisera production. The resulting polyclonal antisera were used in western blot analysis of reduced (with 2-mercaptoethanol) S. neurona lysate to reveal each of the SnSAGs (See, FIG. 3). The mature forms of native SnSAG1 and SnSAG4 are predicted to be approximately 24 kDa, but these antigens co-migrated at approximately 30-32 kDa and correspond to the immunodominant antigen Sn30 that has been described previously (See, FIG. 3) (Granstrom et al., 1993; Liang et al., 1998). SnSAG1 has also been identified by others as a major surface antigen matching the immunodominant Sn30 band (Ellison et al., 2002), but it is apparent that SnSAG4 likely contributes to the antibody reactivity at this molecular weight. The mature form of SnSAG2 is predicted to be about 12 kDa, but this antigen migrated at approximately 18-19 kDa and corresponds to the previously described immunodominant Sn16 antigen (See, FIG. 3) (Granstrom et al., 1993; Liang et al., 1998). Mature SnSAG3 is predicted to be 23 kDa, but migrated at about 28 kDa (See, FIG. 3). The aberrant migration of the SnSAGs under reducing conditions is a characteristic that has been observed previously for the surface antigens of both T. gondii (Burg et al., 1988; Cesbron-Delauw et al., 1994) and N. caninum (Howe et al., 1998). Importantly, the western blot experiments demonstrated that the recombinant forms of the SnSAGs are recognized by antibodies from S. neurona-infected horses. There is strong concordance between antibody recognition of recombinant SnSAG1 (rSnSAG1) and standard western blot analysis of complete parasite antigen (i.e., S. neurona merozoite lysate). Similar results were obtained with rSnSAG2, rSnSAG3, and rSnSAG4. These data demonstrate the utility of using the rSnSAGs in ELISA formats to monitor antibody responses in S. neurona-infected horses.

Enzyme-Linked Immunosorbent Assays (ELISAs) Based on Recombinant S. neurona Surface Antigens (rSnSAGs)

The rSnSAGs expressed in E. coli have been shown in western blots to be recognized by equine antibodies; consequently, these recombinant antigens can be utilized as the key reagents for developing ELISAs based on single S. neurona antigens. An ELISA test was developed for each of the four rSnSAGs that have been identified by the invention.

Expression and Purification of Recombinant SnSAGs.

To produce highly purified recombinant forms of the SnSAGs, the genes for each antigen were cloned into the pET22b expression plasmid from Novagen (Madison, Wis.). This plasmid vector provides a carboxyl-terminal fusion to a 6-residue oligohistidine domain (His-Tag), which binds to metal ion affinity columns and allows for the efficient one-step purification of the expressed recombinant protein. Plasmid constructs were transformed into BL21 DE3) host cells (CodonPlus, Stratagene, Inc.), and expression of recombinant protein was induced by addition of IPTG. Bacterial clones that reliably expressed the recombinant SnSAGs were selected and cyropreserved for future study. The recombinant *S. neurona* surface antigens have been designated rSnSAG1, rSnSAG2, rSnSAG3, and rSnSAG4.

To obtain recombinant protein, the appropriate bacterial clone was grown to logarithmic phase in LB medium, and protein expression was induced by addition of IPTG to the culture. The recombinant protein was extracted from inclusion bodies with 6 M urea and purified from the host cell lysate by $Ni^{++}$-column chromatography according to the manufacturer's protocol (His-Bind resin and buffers, Novagen). Urea was removed by dialysis. If necessary, recombinant proteins was concentrated by centrifugal ultra-filtration in Centricon-10 columns (Amicon).

ELISA Assay

The SN3 strain of *S. neurona* and the Oregon strain of *Neospora hughesi* were maintained by serial passage in bovine turbinate cell monolayers. Upon lysis of the host cell monolayer, zoites were dispersed and filtered (3.0 μm Nucleopore membrane filter, Whatman) to remove debris. Harvested parasites were counted, washed, and stored at –20° C.

Concentration of purified recombinant proteins prepared as described above was determined by a calorimetric assay (Coomassie Plus Protein Assay Reagent, Pierce). Purified rSnSAG1, rSnSAG2, rSnSAG3, and rSnSAG4 were diluted in buffer (0.5 M NaCl and 20 mM Tris-HCl) without urea to final protein concentrations of 8.15 μg/ml, 23.0 μg/ml, 14.56 μg/ml, and 10.3 μg/ml, respectively.

Positive control serum samples were obtained from two horses with histologically confirmed EPM. The negative control sample for all assays was a preinfection serum sample from a weanling used in an experimental infection trial. Thirty six equine serum samples submitted for *S. neurona* serology testing were used for standardization of the rSnSAG ELISAs. The samples had previously been classified as positive or negative by Western blot. Twenty-seven samples from horses of confirmed EPM status were obtained from a collection of the University of Kentucky Gluck Equine Research Center. All cases were confirmed by histological examination of central nervous system tissues for the presence of lesions consistent with EPM, as well as Western blot analysis of CSF fluids. Three equine serum samples from an *S. fayeri* challenge trial were used to examine assay cross-reactivity. An *N. hughesi* positive control serum sample was also evaluated.

Native and recombinant proteins were suspended in SD S-PAGE buffer supplemented with protease inhibitor cocktail (Sigma) and separated on 12% polyacrylamide gels. For Western blot proteins were transferred to nitrocellulose membranes by semi-dry electrophoresis. Membranes were blocked with PBS containing nonfat dry milk, 0.1% Tween 20, and 5% normal goat serum, and incubated for 1 hour in primary antibody solution. The membranes were washed, followed by incubation for 45 min. with horseradish peroxidase-conjugated secondary antibodies (Jackson ImmunoResearch Laboratories, Inc.). Membranes were processed for chemiluminescent detection using SuperSignal substrate (Pierce) and exposed to radiographic film or documented with a FluorChem 8800 imaging system (Alpha Innotech Corp.).

For rSnSAS ELISAs, high-binding 96-well plates (Corning) were incubated overnight at 4° C. with 100 μl purified rSnSAG1, rSnSAG2, rSnSAG3, or rSnSAG4 diluted to 0.20 μg/ml, 1.00 μg/ml, 0.09 μg/ml, and 0.21 μg/ml, respectively. The plates were rinsed with PBS/0.05% Tween 20 and blocked for 1.5 h at room temperature with PBS/1% Tween 20/0.5% normal goat serum/0.001 g/ml nonfat dry milk. Primary sera or CSF was diluted with PBS/1% Tween 20/0.5% normal goat serum/0.001 g/ml nonfat dry milk. One hundred μl aliquots of the sera or CSF containing mixed antibody populations were added to duplicate wells and incubated for 2 h at room temperature. The wells were rinsed, and then incubated for 2 h at room temperature with 150 μl of horseradish peroxidase-conjugated goat anti-horse immunoglobulin G (IgG) secondary antibody (Jackson ImmunoResearch Laboratories, Inc.) diluted to 1:10,000 in PBS/1% Tween 20/0.5% normal goat serum/0.001 g/ml nonfat dry milk. The wells were then again rinsed. The chromogenic substrate o-phenylenediamine dihydrochloride (Sigma) at 0.4 mg/ml (200 μl) was added. After 10 min incubation, the reaction was stopped with 50 μl of 3 M $H_2SO_4$, and $OD_{490}$ was measured in an $E_{max}$ microplate reader (Molecular Devices). To account for interplate variation, the OD of each sample was expressed as a percentage of the high positive standard on the plate.

Figure 6:
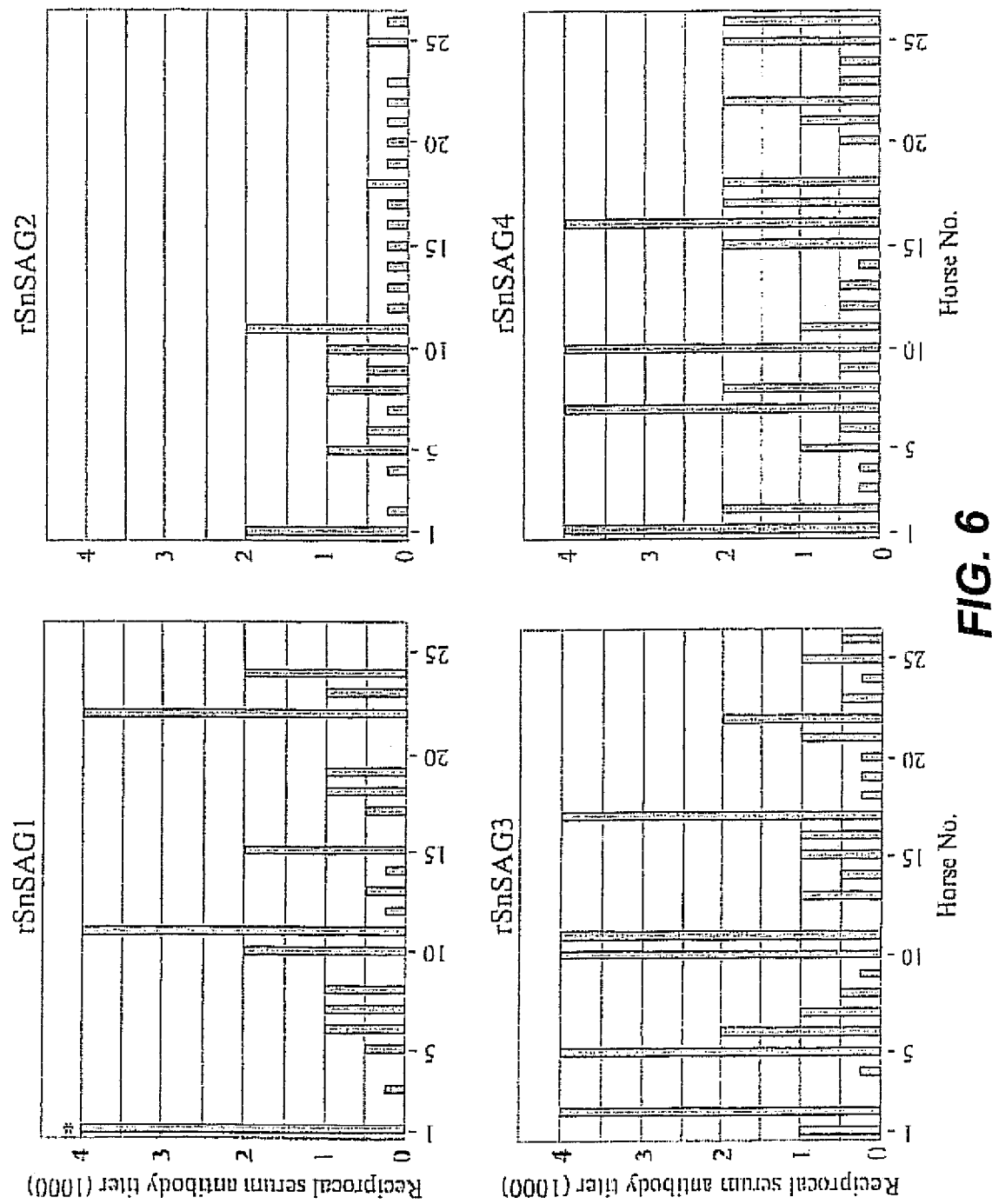
FIG. 6 shows reciprocal antibody titers in serum of EPM-confirmed horses, determined by an ELISA using the recombinant surface antigens of the present invention.
Figure 7:
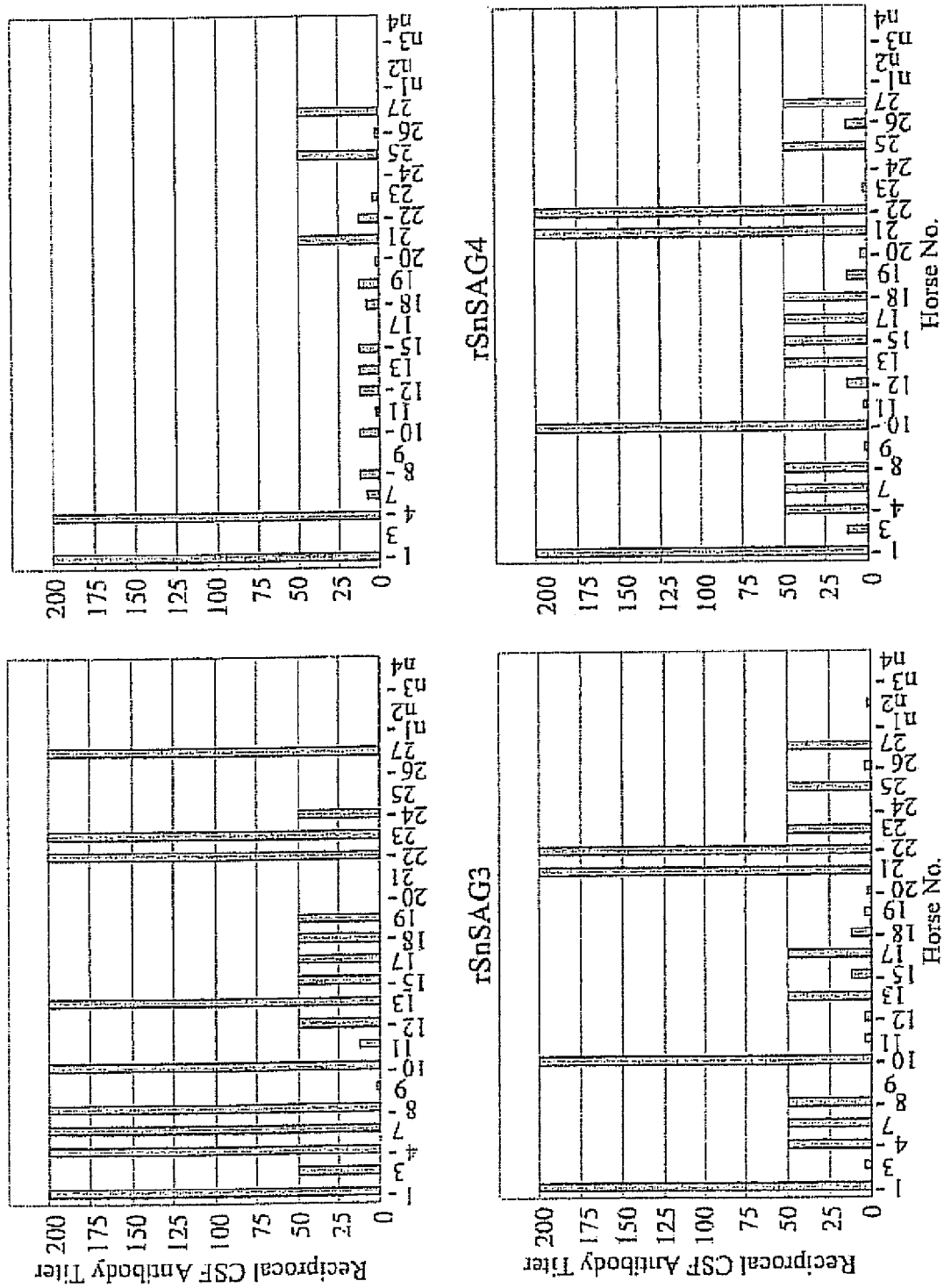
FIG. 7 shows reciprocal antibody titers in CSF of EPM-confirmed horses, determined by an ELISA using the recombinant surface antigens of the present invention.

Serum antibody titers against rSnSAG4 were detected in 25 of 26 (96.2%) EPM-confirmed horses (see FIG. 6). The rSnSAG2 and rSnSAG3 ELISAs yielded seropositive results in 24 of 26 (92.3%) EPM-confirmed horses. Only 18 of the 26 (69.2%) horses had detectable serum antibody titers against rSnSAG1. In total, 18 (81.8%), 18 (81.8%), 20 (90.0%), and 21 (95.5%) of the 22 CSF samples had detectable antibody titers against rSnSAG1, rSnSAG2, rSnSAG3, and rSnSAG4, respectively (see FIG. 7). No significant cross-reactivity of the ELISAs was found when tested against samples containing antibodies to two related pathogens, *S. fayeri* and *S. hughesi* (data not shown).

Figure 8:
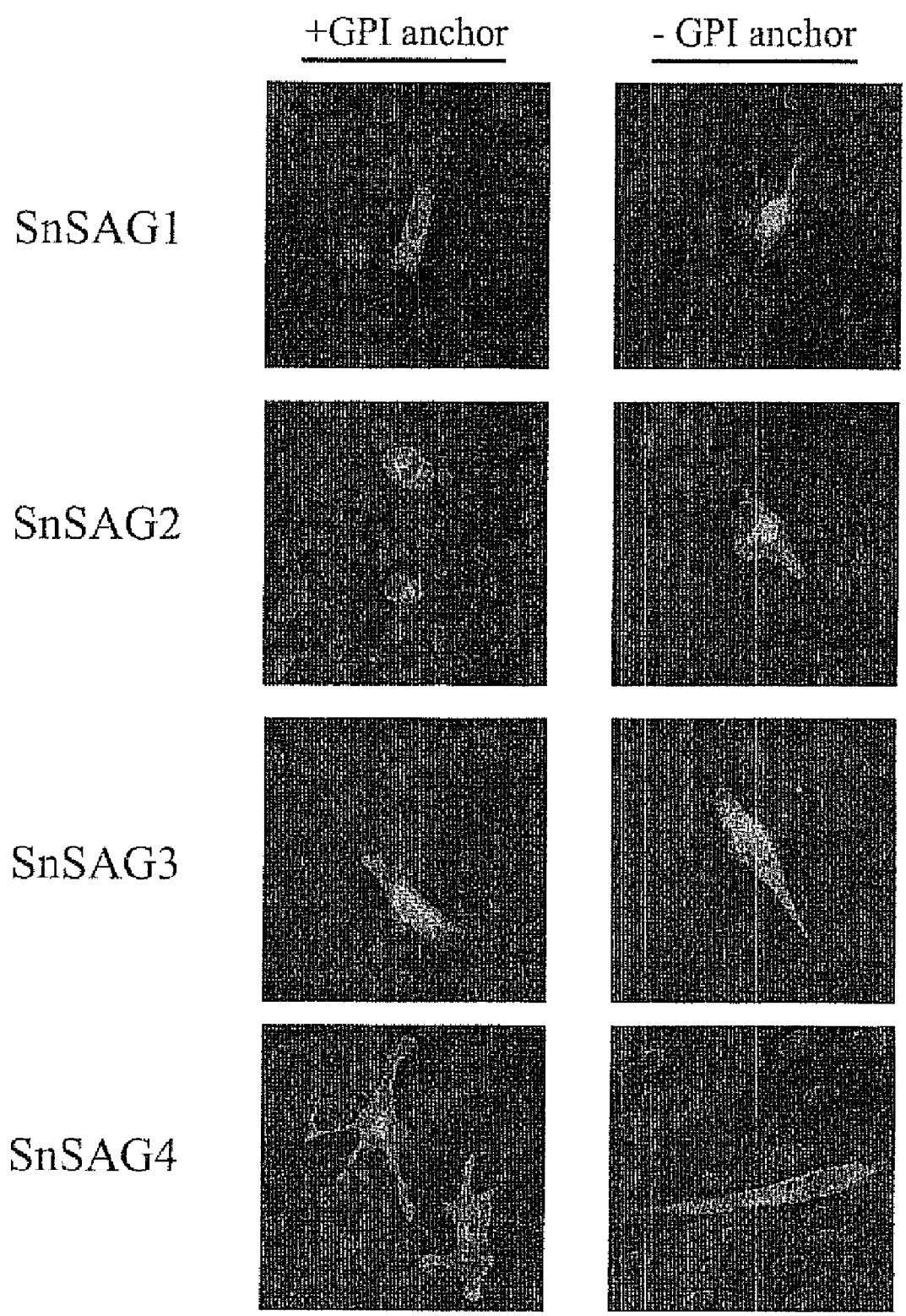
FIG. 8 shows expression of S. neurona surface antigens in COS-1 (green monkey kidney) cells, detected by immunofluorescent labeling with fluorescein isothiocyanate.

Expression of Recombinant *S. neurona* Surface Antigens (rSnSAGs) in Mammalian Cells The open reading frame of each SnSAG as previously described was directionally cloned into the KpnI and XbaI restriction sites of the pVAX1 DNA vaccine plasmid vector (Invitrogen), and the fidelity of the pVAX:SnSAG plasmid constructs was confirmed by expression in COS-1 (green monkey kidney) cells with (+GPI) and without (–GPI) the GPI anchor. Cells were grown on coverslips in 24-well plates. The pVAX:SnSAG plasmids were transfected into the COS-1 cells using the cationic lipid reagent Lipofectamine 2000 (Invitrogen). At 48 hr post-transfection, the coverslips were removed and the cells were fixed with formalin. The cells were then labeled with an anti-rabbit SnSAG serum as appropriate, followed by goat anti-rabbit antibody conjugated to fluorescein isothiocyanate (FITC). Cell nuclei were labeled with DAPI for contrast. As shown in FIG. 8, mammalian cells clearly expressed each transfected surface antigen (SnSAG1, SnSAG2, SnSAG3, and SnSAG4).

Accordingly, a simple, reliable assay is provided for detection of *S. neurona* infection. Importantly, the assays did not cross-react with antisera against related pathogens. The assay described herein provides numerous advantages over current serologic assays, including ease of use, high sample throughput, and more objective interpretation of results. Further, the use of recombinant *S. neurona* surface antigens obviates the need to propagate parasites in tissue culture. Relative to propagation of the parasite in tissue culture, production of the recombinant proteins described herein is inexpensive and simple.

An important tool is therefore provided for detection of *S. neurona* infection, as well as for in-depth examination of the equine humoral response to such infection. For example, combining rSnSAGs in a single ELISA, along with investigation using larger sample sets with more negative controls, may prove useful as serodiagnostic tests due to the high sensitivity and specificity exhibited.

The foregoing descriptions have been presented for purposes of illustration and description. The descriptions are not intended to be exhaustive or to limit the invention to the precise form disclosed. Obvious modifications or variations are possible in light of the above testing. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the claims made in this application when interpreted in accordance with the breadth to which they are fairly, legally and equitably entitled.

What is claimed is:

1. A composition comprising an isolated nucleic acid set forth in the Sequence Listing as SEQ ID NO: 27, and sequences fully complementary thereto.

2. A vector comprising the nucleic acid of claim 1.

3. The vector of claim 2 in a host that expresses a polypeptide encoded by the nucleic acid.

4. The vector of claim 2, wherein the vector is selected from the group consisting of an *Escherichia coli* bacteria and an Alpha virus.

5. The composition of claim 1, wherein the isolated nucleic acid is capable of hybridizing under stringent conditions with a nucleic acid from *Sarcocystis neurona*.

6. The composition of claim 5, wherein the isolated nucleic acid is capable of hybridizing under conditions of low stringency with a nucleic acid from *Sarcocystis neurona*.

7. The composition of claim 5, wherein the isolated nucleic acid is capable of hybridizing under conditions of moderate stringency with a nucleic acid from *Sarcocystis neurona*.

8. The composition of claim 5, wherein the isolated nucleic acid is capable of hybridizing under conditions of high stringency with a nucleic acid from *Sarcocystis neurona*.

9. The composition of claim 1, further comprising a pharmaceutically acceptable carrier.

10. A composition comprising an isolated nucleic acid capable of encoding an antigenic protein from *Sarcocystis neurona*, comprising a nucleotide sequence set forth in the Sequence Listing as SEQ ID NO: 27 and sequences fully complementary thereto.

11. A vector comprising the nucleic acid of claim 10.

12. The vector of claim 11 in a host that expresses the polypeptide encoded by the nucleic acid.

13. The vector of claim 11, wherein the vector is selected from the group consisting of an *Escherichia coli* bacteria and an Alpha virus.

14. An isolated nucleic acid sequence comprising the nucleotide sequence of SEQ ID NO: 27, or a degenerate variant thereof, that encodes a polypeptide comprising the amino acid sequence of SEQ ID NO: 28.

15. A vector comprising the nucleic acid of claim 14.

16. The vector of claim 15 in a host that expresses the polypeptide encoded by the nucleic acid.

17. A composition comprising an immunogenic amount of: (a) an isolated agent comprising a nucleotide sequence set forth in the Sequence Listing as SEQ ID NO: 27 or a degenerate variant thereof that encodes a polypeptide comprising the amino acid sequence set forth in the Sequence Listing as SEQ ID NO: 28; and (b) a pharmaceutically acceptable carrier.

* * * * *

SEQUENCE LISTING

```
<160> NUMBER OF SEQ ID NOS: 38

<210> SEQ ID NO 1
<211> LENGTH: 1148
<212> TYPE: DNA
<213> ORGANISM: Sarcocystis neurona

<400> SEQUENCE: 1
gtgccacaat gccacacaga gcagtcattt tgacatcctc tggaaacctc cctttgcaac     60
tgactggtga acaacgttgt cagcctttcg ctcctctcac gtcaggatga agcggcgttg    120
caacttccga aaagaattag tttccttttt ctggctgttc gtgctgctag gcgcggccaa    180
cgtgtttggg atttacgcgg acgatgagtg ccagcccctg ttggaacacg cagatgatga    240
cacgccaccc gaaaccccta taaggccgga gagaccagtg tcgctgtctg ggtttctcca    300
caaactacta cagcgtggac gtgaacacag gccgaagtct cccgcaagcc gtacggcacg    360
gatgggaagg cagagcgacg acgccaagca aaggcgagca ggggtacttt acacaaacct    420
acttgactac gtgttcgaag cccctgaggt ggaacctaag accacgttct ggggcggcgt    480
taaacagctg cctgctggga gcgtggcgat gactggtttc acgatgttgc ctagatagta    540
cccgccgatg gttggaaaag ttggtcaggt cctgcctgaa acatacacag ccgcgtttgg    600
cgggggttat attgccgtga caggcgacag gagtacagac aatgattata tccctctgcg    660
gactgtcaat tcaaactaac tgctgcgtct cctgcgcctt agccgccttt gttcagccca    720
tatagccggc ggtcctcttt ctttcgtaat gcatggggac tgctgtgaac aagaaggaag    780
acggaggcaa tggggactag gccgccaaca ctagttgagg cactggaact gtgtgcgtgt    840
ctttgttgtt gctgctttca cctgcatggt tgcacgttac agacgggtga ggctcaccta    900
gaacaaggga tcctgcccgc cgcgggtgag tgccggtggg tccaatttta agcgcgcgta    960
gaatgccacg cgttgggctt ggcagatgag acaacaaagt gtggtgacaa atttgcgatc   1020
cgttgcagac cggtagaggc gtagagacga caacctgctc ttgtgctgga aaacagttat   1080
tctgaaagaa ttttctaatg aacagcggct cggcacggtc cgccgaaaac ccgggtgtag   1140
tggtggtc                                                            1148

<210> SEQ ID NO 2
<211> LENGTH: 143
<212> TYPE: PRT
<213> ORGANISM: Sarcocystis neurona

<400> SEQUENCE: 2

Met Lys Arg Arg Cys Asn Phe Arg Lys Glu Leu Val Ser Phe Phe Trp
1               5                   10                  15
```

```
Leu Phe Val Leu Leu Gly Ala Ala Asn Val Phe Gly Ile Tyr Ala Asp
         20                  25                  30

Asp Glu Cys Gln Pro Leu Leu Glu His Ala Asp Asp Thr Pro Pro
         35                  40                  45

Glu Thr Pro Ile Arg Pro Glu Arg Pro Val Ser Leu Ser Gly Phe Leu
 50                  55                  60

His Lys Leu Leu Gln Arg Gly Arg Glu His Arg Pro Lys Ser Pro Ala
 65                  70                  75                  80

Ser Arg Thr Ala Arg Met Gly Arg Gln Ser Asp Asp Ala Lys Gln Arg
                 85                  90                  95

Arg Ala Gly Val Leu Tyr Thr Asn Leu Leu Asp Tyr Val Phe Glu Ala
                100                 105                 110

Pro Glu Val Glu Pro Lys Thr Thr Phe Trp Gly Gly Val Lys Gln Leu
            115                 120                 125

Pro Ala Gly Ser Val Ala Met Thr Gly Phe Thr Met Leu Pro Arg
    130                 135                 140

<210> SEQ ID NO 3
<211> LENGTH: 1393
<212> TYPE: DNA
<213> ORGANISM: Sarcocystis neurona

<400> SEQUENCE: 3
agtattttcc cgcgttttg agagaccaca ctgtgcttcg tttacagtta tgctgaatgt      60
cgcgcagctg ccgcattgtt cggtcgttcg tcagttagca cctattctgg taacgtaacc    120
gcgattacgt atcgcatcaa ctttatcccg attccgtggt ggatgctctt ggcacgtggc    180
ccgcgtccgt agtcggggac gcacgtcttt ttccgtgtcg ttcgtcgtgt tttccctcta    240
catgcgtcaa gactcgccac taagcgcgcc acgagcctca tccgtgaaca actcgaaatg    300
gggaaggcgg tgacaggact tttcctttgc gtgacgctcc ttatttgctg ccgccctgtc    360
agcagcagtg ttttttactta caaccacctc gtccggagta tatttcgaat gcctgacgtg    420
caacacaacc agcagctagc tcagctagcg caaggtgcc tgcaagaagt aaaacgcgct     480
ggccatgagg acgacatcga ggctgcctta gctagtgacg ctgtcgtcaa gtgtcttagt    540
gatttctcgg ttgcgcacgc gcagatgctt ctaccacttc gaaaggatcc ggaaacaatt    600
gcagctctaa aggggccat agcccttgct tcacaagagg actttgctga ggttatccgg     660
gatcgagttc gacgcgatac gtttgtaacg gcctattacg cggacaccga cataaatctg    720
gcgagcccat cgggcaagct tacgtaaatc tggcgagccc attggacaat tctacgaatg    780
ggtggagtgt aaaaaccggt ctgttccttt tatgttacgt gctgtggaca gcgaggtaag    840
gcgtcggtcc gccctagtcc aaagtaaatc atgcaaaagc attcgagaaa tggggaggat    900
gccatgctcc ccatttgggg tgataaatca ccgtttcttt acgggagggc agacaagtag    960
aaggttacgt ttgtactacc tgaacaacga agttactgcg gcttgcagga acggactttg   1020
ctggaaccga cagacggcgc aggaatgcgc ctggtgtttc aactgaaagc agcctccccg   1080
ttaagtgtat gcctgcgaaa tccccacccg gtatcgtgtc atccgcatgt tgtctttgag   1140
cgcgtgagtt gggtgttcat gatgttgggt ctgtcggggt tgacgtttcc tccgtgtgta   1200
cttttataat attgcggcgt ggtgtcgtgt tataaacgct ttgacttctt tggcttacgt   1260
atggtgaatg ttgtgcgaga gagccacgaa ggaatgacac gctggcgcag acatagtact   1320
gtgcgtttcc acttttcaca ctgtggcatt tatgcttctt ccaatgatgc cgaacgtctg   1380
agccacacct ggg                                                      1393
```

-continued

<210> SEQ ID NO 4
<211> LENGTH: 149
<212> TYPE: PRT
<213> ORGANISM: Sarcocystis neurona

<400> SEQUENCE: 4

```
Met Gly Lys Ala Val Thr Gly Leu Phe Leu Cys Val Thr Leu Leu Ile
1               5                   10                  15

Cys Cys Arg Pro Val Ser Ser Ser Val Phe Thr Tyr Asn His Leu Val
            20                  25                  30

Arg Ser Ile Phe Arg Met Pro Asp Val Gln His Asn Gln Gln Leu Ala
        35                  40                  45

Gln Leu Ala Ala Arg Cys Leu Gln Glu Val Lys Arg Ala Gly His Glu
    50                  55                  60

Asp Asp Ile Glu Ala Ala Leu Ala Ser Asp Ala Val Val Lys Cys Leu
65                  70                  75                  80

Ser Asp Phe Ser Val Ala His Ala Gln Met Leu Leu Pro Leu Arg Lys
                85                  90                  95

Asp Pro Glu Thr Ile Ala Ala Leu Lys Gly Ala Ile Ala Leu Ala Ser
            100                 105                 110

Gln Glu Asp Phe Ala Glu Val Ile Arg Asp Arg Val Arg Arg Asp Thr
        115                 120                 125

Phe Val Thr Ala Tyr Tyr Ala Asp Thr Asp Ile Asn Leu Ala Ser Pro
    130                 135                 140

Ser Gly Lys Leu Thr
145
```

<210> SEQ ID NO 5
<211> LENGTH: 973
<212> TYPE: DNA
<213> ORGANISM: Sarcocystis neurona

<400> SEQUENCE: 5

```
agagagagag agaactagtc tcgagttttg ttacttcgca ggtgcttcgc aggtgcttca     60
cattcatatt tcacttgtca ctcaactgcg gcagagtttt cagctctcga agtgcttctg    120
tgtacacaga tttgcacaat tctgttcctc ttcaactacc aacgacgttg cacagcaaaa    180
aaaccttatc aacaatgccg cgagtgtcgc tccttaatct cctggtggtg gcgacggccc    240
ttctcgctgc tggctctacc gtcctgtgcg cggaggaaga tgtaccagga ggtacccttg    300
acacagggag ttccccggga aatccagcga gaccaccgga gaatccacta tggagccgac    360
tgactaaact cgatgcggga ccgctgacga actcattacg gaggcaactg aaaagcgctt    420
cgctcgtgtt ggcgagtctt attgctgcag cgatgttgtc gtccactaat ggaccatttg    480
tggacgcaat ggagatgaat tttacaacgc cactgtagag tcgcataact gctcgaaagg    540
agacagccaa aactagaaaa gagctctctc aaaaggctga gtacctcgtg ggcatcccac    600
aacgaaccgt gtcgacaccg tcgagttctc aagcattgag cagtgattag tcccataatt    660
gatgatcacg gccttagtat cagtttctgt atgcatacac acacgtgctg tttcgctgcg    720
ccctcactta ttgaaattgt tgtgccatcg gtgccattgt cacacctgtg tgttgctggc    780
ccctgcccac gtacacatgt aatcgtaatt cctgtatcgt cggcggtagt gtacgtagct    840
tggctgtacc ctactcgcgt aacaaatttc ctttattgtc tgtggcagtg taacgccaac    900
aagtaaatga tcagcatttt aaggggatac gatacgcgct aaaaaaaaaa aaaaaaaaaa    960
```
aaaaaaaaaa aaa                                                                973

<210> SEQ ID NO 6
<211> LENGTH: 107
<212> TYPE: PRT
<213> ORGANISM: Sarcocystis neurona

<400> SEQUENCE: 6

```
Met Pro Arg Val Ser Leu Leu Asn Leu Leu Val Val Ala Thr Ala Leu
1               5                   10                  15

Leu Ala Ala Gly Ser Thr Val Leu Cys Ala Glu Glu Asp Val Pro Gly
            20                  25                  30

Gly Thr Leu Asp Thr Gly Ser Ser Pro Gly Asn Pro Ala Arg Pro Pro
        35                  40                  45

Glu Asn Pro Leu Trp Ser Arg Leu Thr Lys Leu Asp Ala Gly Pro Leu
    50                  55                  60

Thr Asn Ser Leu Arg Arg Gln Leu Lys Ser Ala Ser Leu Val Leu Ala
65                  70                  75                  80

Ser Leu Ile Ala Ala Ala Met Leu Ser Ser Thr Asn Gly Pro Phe Val
                85                  90                  95

Asp Ala Met Glu Met Asn Phe Thr Thr Pro Leu
            100                 105
```

<210> SEQ ID NO 7
<211> LENGTH: 917
<212> TYPE: DNA
<213> ORGANISM: Sarcocystis neurona

<400> SEQUENCE: 7
ctagtctcga gttttttgtt acttcgcacg tgcttcacat tcatatttca cttgtcgctc        60
aactgtggca gagttttcag ctctcgaagt gcttctgtgt acacagtttt gcacaattct       120
gttcctcttc aactgccaac gacgttgcac agcaaaaaca atcttatcaa caatgccgcg       180
actgtcgctc cttaacctcc tcttggtggc gacggccctt ctcgctgctg gttctaccgt       240
cctgtgcgcg gaggaagatg taccaggagg taaccttgac acagagagtc cgccgggaga       300
tgcagggggg ccaccggtga atccagtacg gagccgagag actgaactcg gagcgcggcc       360
gctgacgaac tcattacgga ggcaactgaa aagcgcttcg ctcgtgttgg cgagtcttat       420
tgctgcagcg atgttgtcgt ccactggtgg accatttgtg gacgcagtgg ggacgaattt       480
tacgtcattg tagagtcgcc taactgctcg acaggagaca gccaaaacta gaaaagagcg       540
ctctcaaaag gctgaatagg ctgatgtggg catcccacac gaaccgtgtc gacaccgagt       600
tctcaaacat tgaacagtga ttagtcccat aattgatgag gatcacggct caagacctct       660
ttctgtatgc atacaggtgc gtgttgcttc gctgagccct tacttattga aattgttgtg       720
ccatcggtgc cagtgtgaca gatgtgtgtt gcttgcctgt gcccacgtac acacggaatc       780
ggaattcctg tctcgtcggc ggtagtgtac gtagctgggc tgcgcccgta ctcgcgtaaa       840
gaattggcgt attttcgatg gcagtgtaac gtcatcgcgt aaatgactat tttaagttaa       900
aaaaaaaaaa aaaaaaa                                                       917

<210> SEQ ID NO 8
<211> LENGTH: 106
<212> TYPE: PRT
<213> ORGANISM: Sarcocystis neurona

<400> SEQUENCE: 8

Met Pro Arg Leu Ser Leu Leu Asn Leu Leu Val Ala Thr Ala Leu
1               5                   10                  15

Leu Ala Ala Gly Ser Thr Val Leu Cys Ala Glu Glu Asp Val Pro Gly
            20                  25                  30

Gly Asn Leu Asp Thr Glu Ser Pro Pro Gly Asp Ala Gly Pro Pro
        35                  40                  45

Val Asn Pro Val Arg Ser Arg Glu Thr Glu Leu Gly Ala Arg Pro Leu
    50                  55                  60

Thr Asn Ser Leu Arg Arg Gln Leu Lys Ser Ala Ser Leu Val Leu Ala
65              70                  75                  80

Ser Leu Ile Ala Ala Met Leu Ser Ser Thr Gly Gly Pro Phe Val
            85                  90                  95

Asp Ala Val Gly Thr Asn Phe Thr Ser Leu
            100                 105

<210> SEQ ID NO 9
<211> LENGTH: 523
<212> TYPE: DNA
<213> ORGANISM: Sarcocystis neurona

<400> SEQUENCE: 9
acttcgcacg tgcttcacat tcatatttca cttgtcgctc aactgtggca gggttttcag      60
cttcgaagt gctttctgtg tacacaaatt tgcacacttc tgttgcactt caactggcaa     120
cgacgttgca cagcaaaaaa accttatcag caatgccgcg actgtcgctc cttaacctcc     180
tggtggtggc gacggccctc ctcgctgctg gctctaccgt cctgtgcgcg gaggaagatg     240
taccagactc aggtggtaac ctttacacag gaagtccgcc gggcgattca gcggggccac     300
agaaggatcc gctacggagc cgacagactg aactcggagc gcgaccgctg acgaactcat     360
tagggagaca actgaagaag ggctcgctct tgttggcgag tctcattatt gctgcagcga     420
tgttgaccga agttggggaa tttgcggatg cgtccatgca taacttcact acaacttttt     480
gaagtcgcgc aaacttcaat ttcctgagag agacagccaa aaa                      523

<210> SEQ ID NO 10
<211> LENGTH: 109
<212> TYPE: PRT
<213> ORGANISM: Sarcocystis neurona

<400> SEQUENCE: 10

Met Pro Arg Leu Ser Leu Leu Asn Leu Leu Val Val Ala Thr Ala Leu
1               5                   10                  15

Leu Ala Ala Gly Ser Thr Val Leu Cys Ala Glu Glu Asp Val Pro Asp
            20                  25                  30

Ser Gly Gly Asn Leu Tyr Thr Gly Ser Pro Pro Gly Asp Ser Ala Gly
        35                  40                  45

Pro Gln Lys Asp Pro Leu Arg Ser Arg Gln Thr Glu Leu Gly Ala Arg
    50                  55                  60

Pro Leu Thr Asn Ser Leu Gly Arg Gln Leu Lys Lys Gly Ser Leu Leu
65              70                  75                  80

Leu Ala Ser Leu Ile Ile Ala Ala Met Leu Thr Glu Val Gly Glu
            85                  90                  95

Phe Ala Asp Ala Ser Met His Asn Phe Thr Thr Thr Phe
            100                 105

<210> SEQ ID NO 11
<211> LENGTH: 994

<210> SEQ ID NO 11
<211> LENGTH: 994
<212> TYPE: DNA
<213> ORGANISM: Sarcocystis neurona

<400> SEQUENCE: 11

```
cgcacgtccg tcacattcat agttcatttg tcgctcaact gtggcagggt tttcagcttt      60
cgaaatactt tctgtgtaca caaatttgca cacttctctt caccttcaac tgacaacgac     120
gtcgcacagc aaaaaaatct tatcaacaat gccgcgcctg tcgctcctta acctcctggt     180
ggtggcgatg gccttcctcg ctgctggctc taccgtactg tgcgcggacg aagatgtaac     240
cggaggtgac gatacagcaa gcccgccgcg agattcagcg cggccaccgg agaatccact     300
acggagccga ttgacggaac tcgtagggcg acggctgatg aactcattag gaagacaagc     360
gacgaacggt tcgctcctgt tggcgagtct tctcattgct gcagcgatgc tcgtcgacat     420
ggggccagtt gcgaacgcgt actcgtacaa catgacacac ccactttaat ttcttgacag     480
gaaacagaca aaacagaaa atagctatcc tcaaaggctg aatacatcac aacggacata     540
gcaacataac ggacgcgtgg acaccgccga ggtcgcaaac gtttcacagt aattggtccg     600
ataattcatg aggattgagg ccttagtacc actttctgta tgcatataca tgattgctgc     660
tttgctgcga atcgttgtg ccatcggtgc cagtgctaca caagtgtgtt gcttgcctgc     720
gccccgtac aaacgtaatc ggaattcctg tatcctctgc ggtggtgtac gtactttcgc     780
ggtgcccgtg cccgcgtaac gaattttccg tcttctctgt tcgcggatgc tctgtgggta     840
ccagctgtgc aagagtgagc aagtgcacaa gacatcgatg aagcatagaa ctacgtcgtt     900
cgcggcaagg catacgcgct gtcactcggt tgtcgcggat gctgtgtggg taccagttgt     960
gcaaaaatta gcaagtgaaa aaaaaaaaaa aaaa                                 994
```

<210> SEQ ID NO 12
<211> LENGTH: 106
<212> TYPE: PRT
<213> ORGANISM: Sarcocystis neurona

<400> SEQUENCE: 12

```
Met Pro Arg Leu Ser Leu Leu Asn Leu Leu Val Val Ala Met Ala Phe
1               5                   10                  15

Leu Ala Ala Gly Ser Thr Val Leu Cys Ala Asp Glu Asp Val Thr Gly
            20                  25                  30

Gly Asp Asp Thr Ala Ser Pro Pro Arg Asp Ser Ala Arg Pro Pro Glu
        35                  40                  45

Asn Pro Leu Arg Ser Arg Leu Thr Glu Leu Val Gly Arg Arg Leu Met
    50                  55                  60

Asn Ser Leu Gly Arg Gln Ala Thr Asn Gly Ser Leu Leu Leu Ala Ser
65                  70                  75                  80

Leu Leu Ile Ala Ala Ala Met Leu Val Asp Met Gly Pro Val Ala Asn
                85                  90                  95

Ala Tyr Ser Tyr Asn Met Thr His Pro Leu
            100                 105
```

<210> SEQ ID NO 13
<211> LENGTH: 822
<212> TYPE: DNA
<213> ORGANISM: Sarcocystis neurona
<220> FEATURE:
<221> NAME/KEY: misc_feature
<222> LOCATION: (746)..(746)
<223> OTHER INFORMATION: n is a, c, g, or t

<400> SEQUENCE: 13

-continued

```
aaacggtcat atttttgcca gttgtcgctc aagtgtagcg gtcgtgcctg cttcgcaagg      60
ccaaactgag ttctacgtac acaaatctgg tcctttcgcc ttcccctcgg tcggcagcgt     120
tgttacgcac cagaacagtc acatcagcaa tgccgcgctt gccgctcctt aagcacctct     180
tggtggccac gttcctcctc gctggtggct ccggcgtcct gtgcggggaa agaggagagc     240
tcggagcaag taaccaccgt ggcggcggga gtgtggatat ccctggagct cctcaggagt     300
cggcagtcgt agaggatggg acagaagcag actcagattt gagatttgag gagcggctcg     360
ccctccatat tgtctcagct gtagccagtg tattgaacac gtttatacgc gacgggaccc     420
cactgagacc aggagtggag aagcgcctgc agtcgccgta tctccgacgt ttggcttatc     480
ccgaggcact tcgactggca atggactatc acatgtaacc tggcgttcgg atgacgcact     540
gttgcggctt ttccgcagtc acggtgcaat cgggaactcc agagggggat gccagcagga     600
aactcgagtg tgggtgggtt ctgtagcagc ggatggttgt cctttctact gaccaatagt     660
cgcaccgcac gaacgctaca agtggcgcca ccagtggtgt ttggtccgtg ttaacggagg     720
aacgactttg tttcagcaac ccccgngcag ccaaacgcac tcgactagtc gctggcgtga     780
acgtgtcaag tcgatgaccc taaaaaaaaa aaaaaaaaaa aa                        822
```

```

<210> SEQ ID NO 14
<211> LENGTH: 122
<212> TYPE: PRT
<213> ORGANISM: Sarcocystis neurona

<400> SEQUENCE: 14

Met Pro Arg Leu Pro Leu Leu Lys His Leu Leu Val Ala Thr Phe Leu
1               5                   10                  15

Leu Ala Gly Gly Ser Gly Val Leu Cys Gly Glu Arg Gly Glu Leu Gly
            20                  25                  30

Ala Ser Asn His Arg Gly Gly Gly Ser Val Asp Ile Pro Gly Ala Pro
        35                  40                  45

Gln Glu Ser Ala Val Val Glu Asp Gly Thr Glu Ala Asp Ser Asp Leu
    50                  55                  60

Arg Phe Glu Glu Arg Leu Ala Leu His Ile Val Ser Ala Val Ala Ser
65                  70                  75                  80

Val Leu Asn Thr Phe Ile Arg Asp Gly Thr Pro Leu Arg Pro Gly Val
                85                  90                  95

Glu Lys Arg Leu Gln Ser Pro Tyr Leu Arg Arg Leu Ala Tyr Pro Glu
            100                 105                 110

Ala Leu Arg Leu Ala Met Asp Tyr His Met
        115                 120

<210> SEQ ID NO 15
<211> LENGTH: 771
<212> TYPE: DNA
<213> ORGANISM: Sarcocystis neurona

<400> SEQUENCE: 15
gttactttgc acgtccttca cattcatgtt tcatttgtcg ctcaactgtc gcagggtttt      60
cagctttcga agtgcttctt gtgtacaaaa atttgcacac tcctgttccc ctttaactgg     120
caaccttgta caccaaaaaa agaaccttat caacgatgcc gcgactgtcg cttcttaacc     180
tcctggtgat ggcgacggcc ctcctcgctg ctggctctac cgtcttgtgc gcggaggaag     240
atgtaacagg aggtgacaat acagcaaacc cgccgcgaaa tccagcgggg ccactggaga     300
```

-continued

```
atccactacg gggcccactg gcggaactcg gagcgcgacg gttgatgaac tcattaggga    360
gacatgtaag gaacggttcg ctcttcttcg cgagtcttat cattgttgca gcgatgctcg    420
tcgactttgt gccagttgcg aacgcgcgca tggacaacgg gacacttgaa ctttaatttc    480
ttgacaggag acggccaaaa gcagaaaaga gctgtcctca aaggctgaat acatcacaac    540
ggacataaca acacaacgga cgcgtggaca ccgccgagtt cggaaacaaa gtaattagtc    600
cgataattca tgagggttga ggccttagta ccactttctg tatggatata catgcttgct    660
gcttcgctgc gcgcttactt atcgaaaatg ctgtgccacc ggtgccagtg ctacacaagt    720
gtgttgcttg cctgcgccca cgtacacacg taatcggaat tcctgtatcg t             771

<210> SEQ ID NO 16
<211> LENGTH: 106
<212> TYPE: PRT
<213> ORGANISM: Sarcocystis neurona

<400> SEQUENCE: 16

Met Pro Arg Leu Ser Leu Leu Asn Leu Leu Val Met Ala Thr Ala Leu
1               5                   10                  15

Leu Ala Ala Gly Ser Thr Val Leu Cys Ala Glu Glu Asp Val Thr Gly
            20                  25                  30

Gly Asp Asn Thr Ala Asn Pro Pro Arg Asn Pro Ala Gly Pro Leu Glu
        35                  40                  45

Asn Pro Leu Arg Gly Pro Leu Ala Glu Leu Gly Ala Arg Arg Leu Met
    50                  55                  60

Asn Ser Leu Gly Arg His Val Arg Asn Gly Ser Leu Phe Phe Ala Ser
65                  70                  75                  80

Leu Ile Ile Val Ala Ala Met Leu Val Asp Phe Val Pro Val Ala Asn
                85                  90                  95

Ala Arg Met Asp Asn Gly Thr Leu Glu Leu
            100                 105

<210> SEQ ID NO 17
<211> LENGTH: 755
<212> TYPE: DNA
<213> ORGANISM: Sarcocystis neurona

<400> SEQUENCE: 17
tgcctgcttc gcaaggccaa actgagttct acgtacacaa atctggtcct ttcgccttcc     60
cctcggtcgg cagcgttgtt acgcaccaga acagtcacat cagcaatgcc gcgcttgccg    120
ctccttaagc acctcttggt ggccacgttc ctcctcgctg gtggctccgg cgtcctgtgc    180
ggggaaagag gagagctcgg agcaagtaac caccgtggcg gcgggagtgt ggatatccct    240
ggagctcctc aggagtcggc agtcgtagag gatgggacag aagcaggtga gcggctgtct    300
cattactgtt aacgcagctg tagcgaatgt gttggacaag attatatgaa gctttttttgc    360 acttgcggtg aaactgggga cgccagcagg aaacttgagt gtgggagaat tctggagcag    420
cgaatggatc tgcttaattg acagcaatcg ttcacaacga cgtgacaact ggtgccttca    480
ggggcgtgtg gtcacagcgc aactatagga gctcggcagt cctcggaatc aatgcgtgaa    540
gctgattacc ctatacacct caaagacgtg gcctcaatcc ctctgctgat acgtatactt    600
ttctgcgtcc tttcgctgag ccgagactca cctgaatctt tggcactgtt gtacgtgtga    660
gttgcttggc tggtcccgta cccatggaat cggaacttct gtaacccagg tggtcgccac    720
gacgataatg tttagctggg cccacactca tctag                               755
```

<210> SEQ ID NO 18
<211> LENGTH: 68
<212> TYPE: PRT
<213> ORGANISM: Sarcocystis neurona

<400> SEQUENCE: 18

Met Pro Arg Leu Pro Leu Leu Lys His Leu Leu Val Ala Thr Phe Leu
1               5                   10                  15

Leu Ala Gly Gly Ser Gly Val Leu Cys Gly Glu Arg Gly Glu Leu Gly
            20                  25                  30

Ala Ser Asn His Arg Gly Gly Gly Ser Val Asp Ile Pro Gly Ala Pro
        35                  40                  45

Gln Glu Ser Ala Val Val Glu Asp Gly Thr Glu Ala Gly Glu Arg Leu
    50                  55                  60

Ser His Tyr Cys
65

<210> SEQ ID NO 19
<211> LENGTH: 811
<212> TYPE: DNA
<213> ORGANISM: Sarcocystis neurona

<400> SEQUENCE: 19
tgcctgcttc gcaaggccaa actgagttct acgtacacaa atctggtcct ttcgccttcc      60
cctcggtcgg cagcgttgtt acgcaccaga acagtcacat cagcaatgcc gcgcttgccg     120
ctccttaagc acctcttggt ggccacgttc ctcctcgctg gtggctccgg cgtcctgtgc     180
ggggaaagag gagagctcgg agcaagtaac ctccgtggcg gcgggagtgt gtatacccct     240
gaagctcctc aggagtcggc agtcgtagag gcagggacag aagaagactc aggagttgcg     300
actctggagt gcgagacgc gttgagtgag gtgggacagg ggatgcggat ggcattgcat      360
ggtatctcaa ctgtagttag cgtattggac ggtgttttag cgacatgtt cccagcgaca      420 gcagaacaga gggagcctat tcagttcccg catctccaac gtttgcttcg tcgactggca     480
atggactaac acgtgtaacc tggcgttcgg atgacgcact gttgcggctt ttccgctgtc     540
acggtgcaat cgggaactcc agaggggat gccagcagga aactcgagtg tgggtgggtt      600
ctgtagcagc ggatggttgt catttctatt gaccaacagt cgcaccgcac gaacgctaca     660
agtggcgcca ccagtggtgt ttggtccgtg tcagcggatg aacgactttg tttcagcaac     720
ccccgcgcag ccaaacgcag tcgacagtcg ctggtgtgaa cgtgtcaagt cgattaaact     780
aaaaaaaaaa aaaaaaaaaa aaaaaaaaaa a                                    811

<210> SEQ ID NO 20
<211> LENGTH: 127
<212> TYPE: PRT
<213> ORGANISM: Sarcocystis neurona

<400> SEQUENCE: 20

Met Pro Arg Leu Pro Leu Leu Lys His Leu Leu Val Ala Thr Phe Leu
1               5                   10                  15

Leu Ala Gly Gly Ser Gly Val Leu Cys Gly Glu Arg Gly Glu Leu Gly
            20                  25                  30

Ala Ser Asn Leu Arg Gly Gly Gly Ser Val Tyr Thr Pro Glu Ala Pro
        35                  40                  45

Gln Glu Ser Ala Val Val Glu Ala Gly Thr Glu Glu Asp Ser Gly Val
    50                  55                  60

```
Ala Thr Leu Glu Leu Arg Asp Ala Leu Ser Glu Val Gly Gln Gly Met
 65                 70                  75                  80

Arg Met Ala Leu His Gly Ile Ser Thr Val Val Ser Val Leu Asp Gly
                85                  90                  95

Val Leu Gly Asp Met Phe Pro Ala Thr Ala Glu Gln Arg Glu Pro Ile
            100                 105                 110

Gln Phe Pro His Leu Gln Arg Leu Leu Arg Arg Leu Ala Met Asp
        115                 120                 125

<210> SEQ ID NO 21
<211> LENGTH: 1493
<212> TYPE: DNA
<213> ORGANISM: Sarcocystis neurona

<400> SEQUENCE: 21
ggggaggtaa gtgttggcgg taatgctgca tcattagggt cagacacgct gtccatctgt      60
cattctcgcc agaatgacga gggcggtgct gctgacgttt ctgacactct gctccgccag     120
agtgtccctt gtgagggccg gagcgccgcc tcaagcaacg tgcgccaatg gcgaaacgac     180
tgttactaag ctcggcagct ctggcgcact acgaatccac tgcccaaata attttcgact     240
cgcgccccgg gctgggaatg acgccggtca gatgcaggtc tatgcaactg cggttgctga     300
gaatcctgta acatacgag acgtcctgcc ggcgcatct tacctctctg tacagaacgt      360 cccgacccte accgtccgc aattgcccgc caaagctacg agcgtctttt ttcactgcca      420
gcagcaaccc gacaaccaat gcttcatcca gtagaagta gcgccggctc cgcgcctagg     480
tccgaatacc tgcgcggcgc tgcagtccac gatcgccttc gaagttcaac aagcgaatga     540
aacagcagtg ttcagctgcg gcgagggact tgctgtgttc ccgcaaggta gcaaagcgtt     600
ggatgaagcc tgctccaaag agcaggccct acccagtggc gccgctttag ctccaaagga     660
tggtgggctc caccttggtt ttcctcagct tcctcagcag gctatgaaga tttgctatat     720
ttgtacgaat ggtggtgtgc aggcagaggc ggcccaacgg tgtgaggttc gcatctccgt     780
cgcagcgaac ccagacggaa gcgttccagg ggctaacgga gccgcctctc taggagctgc     840
cgcacgcagc gcctctgcgt tagggttggc tctcgttgca ggcgctttct tgcactttg     900 ctaatcctgc cgtgtagcgt ctctggtggc ccgccccaca gatcctggtt attcccacag     960
ctgccaaaag gggcaacgac cgctccaaga gcatgcctag acgcgttcag taacgtgcct    1020
actgttccaa acgggaaaa tccgaagatg caaaattcat ccggtgcagc gtcccatgtg    1080
ttcagttacg actggacgag tgtagtcaca tggttttaca tccattcgca gtgcagaggc    1140
gtgggctcgc atattttttt tgtagtgtgc cgttgtagat ccagcaagtt aaatatgtta    1200
ttcattttga gcgcctgttc cacgtaggcg gctggaaaat tttctgggcg ctcgtcggtg    1260
cgccatagca gcaaccagtt agtagcttgc agtgccatga cgcggtctca agatggttca    1320
acagttgcag ttatcagcct ccataggttt taatggcagc gttaccaacg ggctgctttt    1380
caatccagat cgcgtgtcag tttcatatgg aactgggtcc gcagtcgtta tacgaaattt    1440
ggtgtcgaac gatcaaattt tccttcacgg tcaaaaaaaa aaaaaaaaaa aaa           1493

<210> SEQ ID NO 22
<211> LENGTH: 276
<212> TYPE: PRT
<213> ORGANISM: Sarcocystis neurona

<400> SEQUENCE: 22

Met Thr Arg Ala Val Leu Leu Thr Phe Leu Thr Leu Cys Ser Ala Arg
```

-continued

```
1               5                   10                  15
Val Ser Leu Val Arg Ala Gly Ala Pro Pro Gln Ala Thr Cys Ala Asn
            20                  25                  30

Gly Glu Thr Thr Val Thr Lys Leu Gly Ser Ser Gly Ala Leu Arg Ile
        35                  40                  45

His Cys Pro Asn Asn Phe Arg Leu Ala Pro Arg Ala Gly Asn Asp Ala
    50                  55                  60

Gly Gln Met Gln Val Tyr Ala Thr Ala Val Ala Glu Asn Pro Val Asn
65                  70                  75                  80

Ile Arg Asp Val Leu Pro Gly Ala Ser Tyr Leu Ser Val Gln Asn Val
                85                  90                  95

Pro Thr Leu Thr Val Pro Gln Leu Pro Ala Lys Ala Thr Ser Val Phe
            100                 105                 110

Phe His Cys Gln Gln Gln Pro Asp Asn Gln Cys Phe Ile Gln Val Glu
        115                 120                 125

Val Ala Pro Ala Pro Arg Leu Gly Pro Asn Thr Cys Ala Ala Leu Gln
    130                 135                 140

Ser Thr Ile Ala Phe Glu Val Gln Gln Ala Asn Glu Thr Ala Val Phe
145                 150                 155                 160

Ser Cys Gly Glu Gly Leu Ala Val Phe Pro Gln Gly Ser Lys Ala Leu
                165                 170                 175

Asp Glu Ala Cys Ser Lys Glu Gln Ala Leu Pro Ser Gly Ala Ala Leu
            180                 185                 190

Ala Pro Lys Asp Gly Gly Leu His Leu Gly Phe Pro Gln Leu Pro Gln
        195                 200                 205

Gln Ala Met Lys Ile Cys Tyr Ile Cys Thr Asn Gly Gly Val Gln Ala
    210                 215                 220

Glu Ala Ala Gln Arg Cys Glu Val Arg Ile Ser Val Ala Ala Asn Pro
225                 230                 235                 240

Asp Gly Ser Val Pro Gly Ala Asn Gly Ala Ala Ser Leu Gly Ala Ala
                245                 250                 255

Ala Arg Ser Ala Ser Ala Leu Gly Leu Ala Leu Val Ala Gly Ala Phe
            260                 265                 270

Leu His Phe Cys
        275

<210> SEQ ID NO 23
<211> LENGTH: 975
<212> TYPE: DNA
<213> ORGANISM: Sarcocystis neurona

<400> SEQUENCE: 23
atgtaccctt gcggcgagcg gcgttttcag attgtaacgt gacatagtcc tgggtcctct     60
tcagggcagg cgtctcgcag ttgtggtgtc ggtgtacgtg ttcataattt tcacagcctg    120
cttgcagccg tgttggattt ttgctgccaa tatcccaccg tccacgctct caacatggag    180
actccccgat gcattcttgc ctgcgctgca ggcatagcag cagttattat ttgcagttct    240
ttctccgtcg cgtcggccca agtcgcaaca attgcgtgca cacaagctgg aatgacccct    300
gtttctctgg gccccggtca gagctttgtg ctgaactgcc aggcaccctt taccatagcg    360
acgcctgcca actttcacac ccacgcttgt gcgggcactg gtgccaattg tcagaatcct    420
gaaacgtacg ccaagttgtt cccaaaggcg tccaaccacg tgtgggtgag tccagcggac    480
agcactagtg cgactcatac ctggacggca cccgctgcga accagttgag cggcaaaact    540
```

-continued

```
gtgtttagtg tgggatgcac cagtacaggc gacccagccg ggatctgcgc cgtcgacgtg    600
acagtttcca gctcagtgaa gacagtcgct tctggtgtcc tgcttgcaat gtgttcactc    660
gcatctctca cagtgttgta aggtgtgaag atgaaattgt ccccgtgcgg cagagccttc    720
tgaaggtacg taatcggggc ctgggaaggc gtgcaggttt gagatacatc ggtgtacagc    780
acacttgcct tcgttttca aacgcacgaa gtgtgacgta cggtttgaac tctgtgcatc    840
cgaccgtatt ttttgcgcac gtaaccggta cctgcgtccg cgaaacattt tttgctgatt    900
tggtgggaaa gacactattg ctgtttttcg aggccttggc tgatgtgcta aaagggtggg    960
caaaaaaaaa aaaaa                                                    975
```

<210> SEQ ID NO 24
<211> LENGTH: 168
<212> TYPE: PRT
<213> ORGANISM: Sarcocystis neurona

<400> SEQUENCE: 24

```
Met Glu Thr Pro Arg Cys Ile Leu Ala Cys Ala Ala Gly Ile Ala Ala
  1               5                  10                  15

Val Ile Ile Cys Ser Ser Phe Ser Val Ala Ser Ala Gln Val Ala Thr
             20                  25                  30

Ile Ala Cys Thr Gln Ala Gly Met Thr Pro Val Ser Leu Gly Pro Gly
         35                  40                  45

Gln Ser Phe Val Leu Asn Cys Gln Ala Pro Phe Thr Ile Ala Thr Pro
     50                  55                  60

Ala Asn Phe His Thr His Ala Cys Ala Gly Thr Gly Ala Asn Cys Gln
 65                  70                  75                  80

Asn Pro Glu Thr Tyr Ala Lys Leu Phe Pro Lys Ala Ser Asn His Val
                 85                  90                  95

Trp Val Ser Pro Ala Asp Ser Thr Ser Ala Thr His Thr Trp Thr Ala
            100                 105                 110

Pro Ala Ala Asn Gln Leu Ser Gly Lys Thr Val Phe Ser Val Gly Cys
        115                 120                 125

Thr Ser Thr Gly Asp Pro Ala Gly Ile Cys Ala Val Asp Val Thr Val
    130                 135                 140

Ser Ser Ser Val Lys Thr Val Ala Ser Gly Val Leu Leu Ala Met Cys
145                 150                 155                 160

Ser Leu Ala Ser Leu Thr Val Leu
                165
```

<210> SEQ ID NO 25
<211> LENGTH: 1585
<212> TYPE: DNA
<213> ORGANISM: Sarcocystis neurona
<220> FEATURE:
<221> NAME/KEY: misc_feature
<222> LOCATION: (1064)..(1064)
<223> OTHER INFORMATION: n is a, c, g, or t
<220> FEATURE:
<221> NAME/KEY: misc_feature
<222> LOCATION: (1114)..(1114)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1497)..(1497)
<223> OTHER INFORMATION: n is a, c, g, or t
<220> FEATURE:

```
<221> NAME/KEY: misc_feature
<222> LOCATION: (1502)..(1502)
<223> OTHER INFORMATION: n is a, c, g, or t
<220> FEATURE:
<221> NAME/KEY: misc_feature
<222> LOCATION: (1508)..(1508)
<223> OTHER INFORMATION: n is a, c, g, or t
<220> FEATURE:
<221> NAME/KEY: misc_feature
<222> LOCATION: (1510)..(1510)
<223> OTHER INFORMATION: n is a, c, g, or t
<220> FEATURE:
<221> NAME/KEY: misc_feature
<222> LOCATION: (1512)..(1513)
<223> OTHER INFORMATION: n is a, c, g, or t
<220> FEATURE:
<221> NAME/KEY: misc_feature
<222> LOCATION: (1517)..(1517)
<223> OTHER INFORMATION: n is a, c, g, or t
<220> FEATURE:
<221> NAME/KEY: misc_feature
<222> LOCATION: (1520)..(1520)
<223> OTHER INFORMATION: n is a, c, g, or t
<220> FEATURE:
<221> NAME/KEY: misc_feature
<222> LOCATION: (1525)..(1528)
<223> OTHER INFORMATION: n is a, c, g, or t
<220> FEATURE:
<221> NAME/KEY: misc_feature
<222> LOCATION: (1530)..(1530)
<223> OTHER INFORMATION: n is a, c, g, or t
<220> FEATURE:
<221> NAME/KEY: misc_feature
<222> LOCATION: (1533)..(1533)
<223> OTHER INFORMATION: n is a, c, g, or t
<220> FEATURE:
<221> NAME/KEY: misc_feature
<222> LOCATION: (1539)..(1539)
<223> OTHER INFORMATION: n is a, c, g, or t
<220> FEATURE:
<221> NAME/KEY: misc_feature
<222> LOCATION: (1543)..(1545)
<223> OTHER INFORMATION: n is a, c, g, or t
<220> FEATURE:
<221> NAME/KEY: misc_feature
<222> LOCATION: (1550)..(1550)
<223> OTHER INFORMATION: n is a, c, g, or t
<220> FEATURE:
<221> NAME/KEY: misc_feature
<222> LOCATION: (1554)..(1554)
<223> OTHER INFORMATION: n is a, c, g, or t
<220> FEATURE:
<221> NAME/KEY: misc_feature
<222> LOCATION: (1557)..(1558)
<223> OTHER INFORMATION: n is a, c, g, or t

<400> SEQUENCE: 25
catttccccc atcacctgcc gtcaaggacg ttttccctg taaagaccat ttcaatcacc      60
gtgcgtctcc ccctgccttt ctggtctctt acatctgcga agatgatgaa aacttcgttt     120
ctgtcgctcg cagttgcctg ccttgtgtgg gcccctgtac attgcattgc cgcagatcca    180
cctgttgcaa cttgtgtgtc cagggatgac agtccgacac aaacatatca actggcatca    240
attgggcaag tgagaattac atgcccagga ggaactactt tagcaaatag gggggcggag    300
caagccgata acgcccgac ggcagaggtt tactctgaag cggacgctgg gaaaaacgtc    360
gcgttgaata ctttgttggt tggtgggacc tacgttcggg cggacgccaa tgacaacctc    420
acagtctcgc agctgcccac caaagcagtg acggtgcttt tcctctgtaa caggcagcct    480
ggccctggtg ttggatgctg gattgctgtt gaagtcgcgg ctcagcctcc tctgggacca    540
caggcttgta cggttggtgg aagcgaggta acgttgactg taacagctgc aaacgccacc    600
gcccagttcg cctgtgccgc tacgaagaac gtatttccag aaggcacaaa tgtttacaac    660
```

-continued

```
tcggattgta aaacggaaac ccctttaagc actgcattgc caggtgccac gctcacccgt    720
ggaaacatga atgcgctaaa aattcctacg ttgccttcgg ctgcaaagaa cctttgcttc    780
gtgtgtgcaa caaatgttgg ggacgaagcc aaccaaaagt gcagcgttaa aattaatgtg    840
agtggcagcc ctcagggtgg tgggaacggg tccgtgggat tgacagcacg ggctgcctcg    900
gcattaggga ttctcatggt cggagcagcg ttggttcgaa atgtttaagg cggaattacg    960
ctcgccagac ttcacaaact agtccttcta tcgcatgact gagcatgttc ttcatggctg   1020
cttctgtacc gaagtcaccc acgtggtgcg ttaatcagaa tacntgcaga tggtctttgg   1080
ggagaattca cgatttcgtg gatttcacgt gaanacgtgt caacagacgt gcatctggta   1140
ctgatttgtg cattgtcgtc gaanagacgt gtggttggaa acccgggtgc ctttcttgtt   1200
tcgaatccat tcaaggtggt attgtccgta cacaactgta tgtgagtgaa gtggcgaggg   1260
ggaatctgcc aattttgtac actgttgttg tgcgtgtacg ttacgacggc ctcggcgatg   1320
cgtgccacac ccatgtggat tttgattaca ggaaggtgcg cacaaagcag cattttttat   1380
gcggaaacaa tttcgcggat tagactcgcc gccattcatt gcagcatgca gaggcaccgt   1440
gtgggggggg ccttcaagaa acgcttttca agctctcttt tctcctcaaa aaaaccnata   1500
cnctaatnan tnnaaanatn tcacnnnncn tcntatatnc aannnaaaan ctcntgnngg   1560
ggggcccccgt cccaaattcc cctat                                         1585
```

```
<210> SEQ ID NO 26
<211> LENGTH: 281
<212> TYPE: PRT
<213> ORGANISM: Sarcocystis neurona

<400> SEQUENCE: 26
```

Met Met Lys Thr Ser Phe Leu Ser Leu Ala Val Ala Cys Leu Val Trp
1               5                   10                  15

Ala Pro Val His Cys Ile Ala Ala Asp Pro Val Ala Thr Cys Val
                20                  25                  30

Ser Arg Asp Asp Ser Pro Thr Gln Thr Tyr Gln Leu Ala Ser Ile Gly
            35                  40                  45

Gln Val Arg Ile Thr Cys Pro Gly Gly Thr Thr Leu Ala Asn Arg Gly
        50                  55                  60

Ala Glu Gln Ala Asp Asn Gly Pro Thr Ala Glu Val Tyr Ser Glu Ala
65                  70                  75                  80

Asp Ala Gly Lys Asn Val Ala Leu Asn Thr Leu Leu Val Gly Gly Thr
                85                  90                  95

Tyr Val Arg Ala Asp Ala Asn Asp Asn Leu Thr Val Ser Gln Leu Pro
            100                 105                 110

Thr Lys Ala Val Thr Val Leu Phe Leu Cys Asn Arg Gln Pro Gly Pro
        115                 120                 125

Gly Val Gly Cys Trp Ile Ala Val Glu Val Ala Ala Gln Pro Pro Leu
    130                 135                 140

Gly Pro Gln Ala Cys Thr Val Gly Gly Ser Glu Val Thr Leu Thr Val
145                 150                 155                 160

Thr Ala Ala Asn Ala Thr Ala Gln Phe Ala Cys Ala Ala Thr Lys Asn
                165                 170                 175

Val Phe Pro Glu Gly Thr Asn Val Tyr Asn Ser Asp Cys Lys Thr Glu
            180                 185                 190

Thr Pro Leu Ser Thr Ala Leu Pro Gly Ala Thr Leu Thr Arg Gly Asn
        195                 200                 205

```
Met Asn Ala Leu Lys Ile Pro Thr Leu Pro Ser Ala Ala Lys Asn Leu
        210                 215                 220

Cys Phe Val Cys Ala Thr Asn Val Gly Asp Glu Ala Asn Gln Lys Cys
225                 230                 235                 240

Ser Val Lys Ile Asn Val Ser Gly Ser Pro Gln Gly Gly Gly Asn Gly
                245                 250                 255

Ser Val Gly Leu Thr Ala Arg Ala Ala Ser Ala Leu Gly Ile Leu Met
            260                 265                 270

Val Gly Ala Ala Leu Val Arg Asn Val
        275                 280

<210> SEQ ID NO 27
<211> LENGTH: 1111
<212> TYPE: DNA
<213> ORGANISM: Sarcocystis neurona
<220> FEATURE:
<221> NAME/KEY: misc_feature
<222> LOCATION: (267)..(267)
<223> OTHER INFORMATION: n is a, c, g, or t

<400> SEQUENCE: 27
gaggtgaagt attaatgcca cgtactgctg tttcgtatgc tacctgtcaa taccatacct      60
cggcgtcacc ctattgggaa cagtttccat cgaaaatgtt acgtgcgaca gtgttacgcg     120
cgacacttgt tgctactgcg gttatatacc ttgccggtcg tttacaatac gtcgtagcac     180
ggaaccccga gcaggctaca tgcgttctcg ggcaagcaac agcggtaaca gagcttgtaa     240
cattcggtgg cctcaatatt gtatgcncta acggttccac tttgcaacag gttcctgcgg     300
ccccaggggc ggccgacggg gcccagggcg cgggatatgt tttttcctca gatcaggaga     360
accgacaggg agtagttctc gaacaagtgg tgcctggggc tatcttcgca gtagggcaaa     420
ataatcagcc caacgttttg aacgtcgcgc agctgccctc ggcgcccag agcatttact      480
ttctgtgtcg tccacaagag aacgaacaac agacttgctt tatacgcgtg aatattcccg     540
cctcgcctcc tttgggaccg aatgcgtgtg tcgtacacaa taccgaggta cagttcaagg     600
cgggatccag caacgccacc gtccagttct cctgcggcaa cgccgcagca ctgcaaccac     660
aacaggctac taaattttc gaccaaactt gtcagcaaga actggagcta gacacagtga     720
ccctggtgc gacgtgccag cggcctgcgg caggggat ggttacagtg acgttcccgc       780
gcctgccgcc acaaaatcgg aaactctgct ttgtctgcac ccgcggacaa gagaattgca     840
aggttattat cgatgtagca gcggacccgg ccggtggtgc agctgtgggg atcacagctc     900
gtaccgcgtc ggcattgggt atcgtcgtcg ctgcagcagg cctcgtcggt gtgttctaac     960
ttcccgttcg cagagtcaac ggttgagtgg ttcttgtgga dacagccatt tgaataggtg    1020
gtggacggct gaaaggaaca gcttcgtcgc atggggagct gattatcgtt tcagcctaaa    1080
ctattggtgg accaaaaaaa aaaaaaaaaa a                                   1111

<210> SEQ ID NO 28
<211> LENGTH: 287
<212> TYPE: PRT
<213> ORGANISM: Sarcocystis neurona
<220> FEATURE:
<221> NAME/KEY: misc_feature
<222> LOCATION: (58)..(58)
<223> OTHER INFORMATION: Xaa can be any naturally occurring amino acid

<400> SEQUENCE: 28

Met Leu Arg Ala Thr Val Leu Arg Ala Thr Leu Val Ala Thr Ala Val
```

```
                1               5                  10                 15
Ile Tyr Leu Ala Gly Arg Leu Gln Tyr Val Val Ala Arg Asn Pro Glu
                    20                  25                  30

Gln Ala Thr Cys Val Leu Gly Gln Ala Thr Ala Val Thr Glu Leu Val
                    35                  40                  45

Thr Phe Gly Gly Leu Asn Ile Val Cys Xaa Asn Gly Ser Thr Leu Gln
                    50                  55                  60

Gln Val Pro Ala Ala Pro Gly Ala Ala Asp Gly Ala Gln Gly Ala Gly
 65                 70                  75                  80

Tyr Val Phe Ser Ser Asp Gln Glu Asn Arg Gln Gly Val Val Leu Glu
                    85                  90                  95

Gln Val Val Pro Gly Ala Ile Phe Ala Val Gly Gln Asn Asn Gln Pro
                   100                 105                 110

Asn Val Leu Asn Val Ala Gln Leu Pro Ser Ala Pro Gln Ser Ile Tyr
                   115                 120                 125

Phe Leu Cys Arg Pro Gln Glu Asn Glu Gln Gln Thr Cys Phe Ile Arg
                   130                 135                 140

Val Asn Ile Pro Ala Ser Pro Pro Leu Gly Pro Asn Ala Cys Val Val
145                150                 155                 160

His Asn Thr Glu Val Gln Phe Lys Ala Gly Ser Ser Asn Ala Thr Val
                   165                 170                 175

Gln Phe Ser Cys Gly Asn Ala Ala Ala Leu Gln Pro Gln Gln Ala Thr
                   180                 185                 190

Lys Ile Phe Asp Gln Thr Cys Gln Gln Glu Leu Glu Leu Asp Thr Val
                   195                 200                 205

Thr Pro Gly Ala Thr Cys Gln Arg Pro Ala Ala Gly Gly Met Val Thr
                   210                 215                 220

Val Thr Phe Pro Arg Leu Pro Pro Gln Asn Arg Lys Leu Cys Phe Val
225                230                 235                 240

Cys Thr Arg Gly Gln Glu Asn Cys Lys Val Ile Ile Asp Val Ala Ala
                   245                 250                 255

Asp Pro Ala Gly Gly Ala Ala Val Gly Ile Thr Ala Arg Thr Ala Ser
                   260                 265                 270

Ala Leu Gly Ile Val Val Ala Ala Gly Leu Val Gly Val Phe
                   275                 280                 285

<210> SEQ ID NO 29
<211> LENGTH: 1342
<212> TYPE: DNA
<213> ORGANISM: Sarcocystis neurona

<400> SEQUENCE: 29
cgtctcactg cctacttcta gaattatggg ataaggctca cccgatctcc ttctcataga      60
aagtaacttg cgtgttgcgg ctgcggtgga atcctggtat ctgcggtgaa attaccaacg     120
ctcctcgttg tcagcctgga gctgcgcacc aacgacttt tgcgctgcaa cagtgaacgc     180
gccagcagtc ctcgcgtttc cgggaagggc tcggcaattc tgcgtccgtt tttcagggtc     240
agcgggaacc atcatggcga actttgctct tcgctttgtc gcttttgtaa tcgtgtccgt     300
gttccacttg tgctcaagac ctgttcatgc gtcttttgaa accttcctaa cggcgcccat     360
aatacagtac ggcctctcag gatatccgct tgcggtgagg cactacattg cgtggctgga     420
tgtaatacaa caatgccaac ctccaactgt agatcgtgca ttgcagaccc aagaaggtca     480
ggaggcgtac actaaggctg ttgttgccgt gctactgggc gcactggatg aaggcgttaa     540
```

-continued

```
tgtacagcat aaggaattt t acatgcagct cctgaagaac atacagagcg gcgccttctt      600
gaaggcgtta agagatgaga gtcagagagc catccttcag gagtacctag acaagaaggg      660
aagaagccgg ctcccccaag gattctcaaa taaggctgtt caaaccgcat acacgtggg       720 ggttcttctg gtgacttgtg tcgcgttgcc gttggtatta atgcattaaa atccacttat      780
cccacctttc gtttacgtgc gaacatcaaa cggaagtcgt tgacggtgga gggcgtttct      840 ttccggggc ttgagtccgc tcgtatccgt gcgttcctcg ccggttcaca catttgtgta       900
gagacctttt cgcctgaagt tctgaatgtc gttatggcct attccgttca gacgcgaact      960
tgcgacgagt gtctgttcga tcaagcgcgg tccgcactgt gtgacgcagc gaatccgcac     1020
agaggaagat gggggacgta atgggtgaac ccggaaaact ctttacggag agcgcatttt     1080
cgttgatgcc atttctaagt gtgtaacctc cttttggtgc gttgccacac attcgtaact     1140
gagggtactc ttacgtgcat ttcaccccctg tctcggaaag gttggggttg taacttgtgg    1200
acacggaaat cttttacgg agaaagtatc tcttttcatg tcacttccgc ctctgtaacc     1260
ctcttttggg gggtggccaa acacgcgcaa ctgaggttat tgttacgtcc aaaaaaaaaa    1320
aaaaaaaaaa aaaaaaaaaa aa                                             1342
```

<210> SEQ ID NO 30
<211> LENGTH: 171
<212> TYPE: PRT
<213> ORGANISM: Sarcocystis neurona

<400> SEQUENCE: 30

```
Met Ala Asn Phe Ala Leu Arg Phe Val Ala Phe Val Ile Val Ser Val
1               5                   10                  15

Phe His Leu Cys Ser Arg Pro Val His Ala Ser Phe Glu Thr Phe Leu
            20                  25                  30

Thr Ala Pro Ile Ile Gln Tyr Gly Leu Ser Gly Tyr Pro Leu Ala Val
        35                  40                  45

Arg His Tyr Ile Ala Trp Leu Asp Val Ile Gln Gln Cys Gln Pro Pro
    50                  55                  60

Thr Val Asp Arg Ala Leu Gln Thr Gln Glu Gly Gln Glu Ala Tyr Thr
65                  70                  75                  80

Lys Ala Val Val Ala Val Leu Leu Gly Ala Leu Asp Glu Gly Val Asn
                85                  90                  95

Val Gln His Lys Glu Phe Tyr Met Gln Leu Leu Lys Asn Ile Gln Ser
            100                 105                 110

Gly Ala Phe Leu Lys Ala Leu Arg Asp Glu Ser Gln Arg Ala Ile Leu
        115                 120                 125

Gln Glu Tyr Leu Asp Lys Lys Gly Arg Ser Arg Leu Pro Gln Gly Phe
    130                 135                 140

Ser Asn Lys Ala Val Gln Thr Ala Ser His Val Gly Val Leu Leu Val
145                 150                 155                 160

Thr Cys Val Ala Leu Pro Leu Val Leu Met His
                165                 170
```

<210> SEQ ID NO 31
<211> LENGTH: 240
<212> TYPE: PRT
<213> ORGANISM: Sarcocystis neurona

<400> SEQUENCE: 31

```
Arg Val Ser Leu Val Arg Ala Gly Ala Pro Pro Gln Ala Thr Cys Ala
1               5                   10                  15
```

```
Asn Gly Glu Thr Thr Val Thr Lys Leu Gly Ser Ser Gly Ala Leu Arg
            20                  25                  30

Ile His Cys Pro Asn Asn Phe Arg Leu Ala Pro Arg Ala Gly Asn Asp
            35                  40                  45

Ala Gly Gln Met Gln Val Tyr Ala Thr Ala Val Ala Glu Asn Pro Val
            50                  55                  60

Asn Ile Arg Asp Val Leu Pro Gly Ala Ser Tyr Leu Ser Val Gln Asn
65                  70                  75                  80

Val Pro Thr Leu Thr Val Pro Gln Leu Pro Ala Lys Ala Thr Ser Val
                    85                  90                  95

Phe Phe His Cys Gln Gln Gln Pro Asp Asn Gln Cys Phe Ile Gln Val
            100                 105                 110

Glu Val Ala Pro Ala Pro Arg Leu Gly Pro Asn Thr Cys Ala Ala Leu
            115                 120                 125

Gln Ser Thr Ile Ala Phe Glu Val Gln Gln Ala Asn Glu Thr Ala Val
            130                 135                 140

Phe Ser Cys Gly Glu Gly Leu Ala Val Phe Pro Gln Gly Ser Lys Ala
145                 150                 155                 160

Leu Asp Glu Ala Cys Ser Lys Glu Gln Ala Leu Pro Ser Gly Ala Ala
                    165                 170                 175

Leu Ala Pro Lys Asp Gly Gly Leu His Leu Gly Phe Pro Gln Leu Pro
            180                 185                 190

Gln Gln Ala Met Lys Ile Cys Tyr Ile Cys Thr Asn Gly Gly Val Gln
            195                 200                 205

Ala Glu Ala Ala Gln Arg Cys Glu Val Arg Ile Ser Val Ala Ala Asn
            210                 215                 220

Pro Asp Gly Ser Val Pro Gly Ala Asn Gly Ala Ser Leu Gly Ala
225                 230                 235                 240

<210> SEQ ID NO 32
<211> LENGTH: 232
<212> TYPE: PRT
<213> ORGANISM: Sarcocystis neurona

<400> SEQUENCE: 32

Arg Asn Pro Glu Gln Ala Thr Cys Val Leu Gly Gln Ala Thr Ala Val
1               5                   10                  15

Thr Glu Leu Val Thr Phe Gly Leu Asn Ile Val Cys Pro Asn Gly
            20                  25                  30

Ser Thr Leu Gln Gln Val Pro Ala Ala Pro Gly Ala Ala Asp Gly Ala
            35                  40                  45

Gln Gly Ala Gly Tyr Val Phe Ser Ser Asp Gln Glu Asn Arg Gln Gly
            50                  55                  60

Val Val Leu Glu Gln Val Pro Gly Ala Ile Phe Ala Val Gly Gln
65                  70                  75                  80

Asn Asn Gln Pro Asn Val Leu Asn Val Ala Gln Leu Pro Ser Ala Pro
                    85                  90                  95

Gln Ser Ile Tyr Phe Leu Cys Arg Pro Gln Glu Asn Glu Gln Gln Thr
            100                 105                 110

Cys Phe Ile Arg Val Asn Ile Pro Ala Ser Pro Leu Gly Pro Asn
            115                 120                 125

Ala Cys Val Val His Asn Thr Glu Val Gln Phe Lys Ala Gly Ser Ser
            130                 135                 140

Asn Ala Thr Val Gln Phe Ser Cys Gly Asn Ala Ala Ala Leu Gln Pro
```

```
                145                 150                 155                 160
Gln Gln Ala Thr Lys Ile Phe Asp Gln Thr Cys Gln Gln Glu Leu Glu
                165                 170                 175

Leu Asp Thr Val Thr Pro Gly Ala Thr Cys Gln Arg Pro Ala Ala Gly
            180                 185                 190

Gly Met Val Thr Val Thr Phe Pro Arg Leu Pro Gln Asn Arg Lys
            195                 200                 205

Leu Cys Phe Val Cys Thr Arg Gly Gln Glu Asn Cys Lys Val Ile Ile
        210                 215                 220

Asp Val Ala Ala Asp Pro Ala Gly
225                 230

<210> SEQ ID NO 33
<211> LENGTH: 226
<212> TYPE: PRT
<213> ORGANISM: Sarcocystis neurona

<400> SEQUENCE: 33

Ile Ala Ala Asp Pro Pro Val Ala Thr Cys Val Ser Arg Asp Asp Ser
1               5                   10                  15

Pro Thr Gln Thr Tyr Gln Leu Ala Ser Ile Gly Gln Val Arg Ile Thr
            20                  25                  30

Cys Pro Gly Gly Thr Thr Leu Ala Asn Arg Gly Ala Glu Gln Ala Asp
        35                  40                  45

Asn Gly Pro Thr Ala Glu Val Tyr Ser Glu Ala Asp Ala Gly Lys Asn
    50                  55                  60

Val Ala Leu Asn Thr Leu Val Gly Gly Thr Tyr Val Arg Ala Asp
65                  70                  75                  80

Ala Asn Asp Asn Leu Thr Val Ser Gln Leu Pro Thr Lys Ala Val Thr
                85                  90                  95

Val Leu Phe Leu Cys Asn Arg Gln Pro Gly Pro Gly Val Gly Cys Trp
            100                 105                 110

Ile Ala Val Glu Val Ala Ala Gln Pro Pro Leu Gly Pro Gln Ala Cys
        115                 120                 125

Thr Val Gly Gly Ser Glu Val Thr Leu Thr Val Thr Ala Ala Asn Ala
    130                 135                 140

Thr Ala Gln Phe Ala Cys Ala Thr Lys Asn Val Phe Pro Glu Gly
145                 150                 155                 160

Thr Asn Val Tyr Asn Ser Asp Cys Lys Thr Glu Thr Pro Leu Ser Thr
                165                 170                 175

Ala Leu Pro Gly Ala Thr Leu Thr Arg Gly Asn Met Asn Ala Leu Lys
            180                 185                 190

Ile Pro Thr Leu Pro Ser Ala Ala Lys Asn Leu Cys Phe Val Cys Ala
        195                 200                 205

Thr Asn Val Gly Asp Glu Ala Asn Gln Lys Cys Ser Val Lys Ile Asn
    210                 215                 220

Val Ser
225

<210> SEQ ID NO 34
<211> LENGTH: 231
<212> TYPE: PRT
<213> ORGANISM: Sarcocystis muris

<400> SEQUENCE: 34

Ser Asn Val Ser Ser Thr Leu Gln Cys Asp Lys Thr Asn Lys Arg Leu
```

```
                    1               5                  10                 15

Ala Thr Glu Thr Ile Ser Thr Pro Gln Ala Thr Leu Lys Leu Ala Cys
                   20                  25                 30

Pro Ser Ser Thr Thr Phe Leu Pro Thr Tyr Gly Asp Ala Gly Thr
            35                  40                 45

Gln Thr Val Tyr Leu Thr Gln Asp Gly Ser Ser Thr Glu Lys Leu Gln
            50                  55                 60

Thr Ala Leu Pro Gly Ala Thr Ala Lys Gln Glu Asp Ser Gln Thr Asn
65                   70                  75                  80

Glu Met Thr Leu Thr Phe Pro Gln Leu Pro Asp Thr Ser Gln Thr Val
                    85                  90                  95

Tyr Phe His Cys Leu Gly Thr Glu Asn Ile Ala Gly Gln Gly Ser Arg
                100                 105                110

Lys Glu Val Cys Gly Phe Ala Val Thr Leu Thr Ala Pro Pro Gln
            115                 120                125

Gly Pro Gln Ala Cys Val Val Pro Gly Thr Thr Ile Arg Leu Gly Ile
        130                 135                140

Ala Asn Glu Gly Asp Thr Thr Arg Phe Thr Cys Gly Gly Asp Leu Lys
145                 150                 155                160

Leu Ser Pro Thr Ala Ala Asp Lys Val Phe Lys Glu Asp Cys Ser Thr
                165                 170                 175

Glu Glu Ser Leu Lys Asp Leu Lys Arg Ser Glu Asp Lys Asn Ser Tyr
                180                 185                 190

Phe Val Leu Thr Ala Thr Lys Thr Pro Ser Lys Thr Thr His Cys Tyr
                195                 200                 205

Leu Cys Glu Pro Asp Pro Thr Lys Lys Gly His Asn Asp Lys Asn Cys
        210                 215                 220

Ala Val Leu Ile Ala Val Gly
225                 230

<210> SEQ ID NO 35
<211> LENGTH: 267
<212> TYPE: PRT
<213> ORGANISM: Toxoplasma gondii

<400> SEQUENCE: 35

Gln Asp Asp Gly Glu Gly Ser Val Val Tyr Ser Asp Thr Gly Thr Val
1               5                  10                 15

Cys Asp Val Ala Ala Gly Thr Lys Leu Val Ile Val Glu Lys Pro Gly
                20                  25                 30

Thr Val Lys Phe Lys Cys Gly Ala Ser Leu Pro Thr Leu Tyr Pro Ala
            35                  40                 45

Gln Asn Ser Ala Asp Gln Thr Val Cys Asp Tyr Pro Asn Cys Arg Thr
        50                  55                  60

Pro Val Lys Leu Ala Asp Leu Phe Asp Gly Ala Ser Leu Thr Lys Glu
65                   70                  75                  80

Thr Val Ser Glu Gly Val Glu Tyr Ser Phe Thr Thr Ser Lys Trp Pro
                85                  90                  95

Asp Ser Ala Gly Ser Ile Phe Phe Ser Cys Lys Pro Asn Pro Pro Thr
                100                 105                 110

Pro Pro Ser Ala Leu Arg Gln Ala Glu Glu Asp Pro Gln Ser Thr Thr
            115                 120                 125

Ser Ala Ala Asp Ala Cys Thr Val Arg Ile Gly Ile Arg Gly Lys Pro
        130                 135                 140
```

Glu Lys Glu Ile Pro Ser Tyr Glu Cys Ser Thr Pro Thr Gly Gln Arg
145                 150                 155                 160

Phe Phe Arg Val Asp Ser Ser Gly Asp Ala Val Ser Phe Ser Cys Gly
                165                 170                 175

Ala Glu Met Ala Leu Glu Thr Gln Thr His Ala Tyr Gln Thr Ala Glu
            180                 185                 190

Cys Thr Asp Leu Thr Pro Leu Thr Thr Leu Leu Pro Ser Ala Ser Leu
        195                 200                 205

Thr Gln Asp Thr Ser Gln Ser Gly Thr Leu Glu Asn Pro Leu Tyr Thr
    210                 215                 220

Leu Thr Val Pro Gln Leu Pro Gly Glu Pro Ile Asn Gln Leu Cys Phe
225                 230                 235                 240

Leu Cys Lys Ser Lys Glu Ser Ser Ser Thr Pro Asp Val Cys Lys
                245                 250                 255

Val Leu Ile Gly Phe Glu Thr Leu Pro Asn Asp
            260                 265

<210> SEQ ID NO 36
<211> LENGTH: 118
<212> TYPE: PRT
<213> ORGANISM: Sarcocystis neurona

<400> SEQUENCE: 36

Gln Val Ala Thr Ile Ala Cys Thr Gln Ala Gly Met Thr Pro Val Ser
1               5                   10                  15

Leu Gly Pro Gly Gln Ser Phe Val Leu Asn Cys Gln Ala Pro Phe Thr
            20                  25                  30

Ile Ala Thr Pro Ala Asn Phe His Thr His Ala Cys Ala Gly Thr Gly
        35                  40                  45

Ala Asn Cys Gln Asn Pro Glu Thr Tyr Ala Lys Leu Phe Pro Lys Ala
    50                  55                  60

Ser Asn His Val Trp Val Ser Pro Ala Asp Ser Thr Ser Ala Thr His
65                  70                  75                  80

Thr Trp Thr Ala Pro Ala Ala Asn Gln Leu Ser Gly Lys Thr Val Phe
                85                  90                  95

Ser Val Gly Cys Thr Ser Thr Gly Asp Pro Ala Gly Ile Cys Ala Val
            100                 105                 110

Asp Val Thr Val Ser Ser
        115

<210> SEQ ID NO 37
<211> LENGTH: 263
<212> TYPE: PRT
<213> ORGANISM: Toxoplasma gondii

<400> SEQUENCE: 37

Ser Asp Pro Pro Leu Val Ala Asn Gln Val Thr Cys Pro Asp Lys
1               5                   10                  15

Lys Ser Thr Ala Ala Val Ile Leu Thr Pro Thr Glu Asn His Phe Thr
            20                  25                  30

Leu Lys Cys Pro Lys Thr Ala Leu Thr Glu Pro Pro Thr Leu Ala Tyr
        35                  40                  45

Ser Pro Asn Arg Gln Ile Cys Pro Ala Gly Thr Thr Ser Ser Cys Thr
    50                  55                  60

Ser Lys Ala Val Thr Leu Ser Ser Leu Ile Pro Glu Ala Glu Asp Ser
65                  70                  75                  80

Trp Trp Thr Gly Asp Ser Ala Ser Leu Asp Thr Ala Gly Ile Lys Leu
                85                  90                  95

Thr Val Pro Ile Glu Lys Phe Pro Val Thr Thr Gln Thr Phe Val Val
            100                 105                 110

Gly Cys Ile Lys Gly Asp Asp Ala Gln Ser Cys Met Val Thr Val Thr
        115                 120                 125

Val Gln Ala Arg Ala Ser Ser Val Val Asn Asn Val Ala Arg Cys Ser
130                 135                 140

Tyr Gly Ala Asn Ser Thr Leu Gly Pro Val Lys Leu Ser Ala Glu Gly
145                 150                 155                 160

Pro Thr Thr Met Thr Leu Val Cys Gly Lys Asp Gly Val Lys Val Pro
                165                 170                 175

Gln Asp Asn Asn Gln Tyr Cys Ser Gly Thr Thr Leu Thr Gly Cys Asn
            180                 185                 190

Glu Lys Ser Phe Lys Asp Ile Leu Pro Lys Leu Ser Glu Asn Pro Trp
        195                 200                 205

Gln Gly Asn Ala Ser Ser Asp Asn Gly Ala Thr Leu Thr Ile Asn Lys
210                 215                 220

Glu Ala Phe Pro Ala Glu Ser Lys Ser Val Ile Ile Gly Cys Thr Gly
225                 230                 235                 240

Gly Ser Pro Glu Lys His His Cys Thr Val Gln Leu Glu Phe Ala Gly
                245                 250                 255

Ala Ala Gly Ser Ala Lys Ser
            260

<210> SEQ ID NO 38
<211> LENGTH: 296
<212> TYPE: PRT
<213> ORGANISM: Toxoplasma gondii

<400> SEQUENCE: 38

Gly Pro Pro Tyr Arg Tyr Glu Pro Glu Lys Phe Thr Cys Arg Pro Lys
1               5                   10                  15

Lys Gly Ile Leu Ser Gln Trp Val Ser Leu Leu Tyr Gln Val Gln His
            20                  25                  30

Asn Ile Thr Phe Ala Cys Glu Glu Ala Thr Pro Val Pro Thr Thr Leu
        35                  40                  45

Ile Ser Glu Glu His Gly Leu Met Val Cys Ala Glu Asn Met Thr Pro
    50                  55                  60

Glu Glu Cys Glu Ala Asn Pro Ala Pro Leu Ser Ala Phe Leu Pro Gly
65                  70                  75                  80

Ala Thr Lys Glu Trp Val Thr Gly Asp Ser Val Leu Thr Gly Leu Lys
                85                  90                  95

Ile Ser Val Pro Glu Ser Gln Tyr Pro Ala Asn Ala Lys Ser Phe Arg
            100                 105                 110

Val Gly Cys Arg His Asn Thr Lys Thr Gly Asn Thr Cys Met Leu Thr
        115                 120                 125

Ile His Val Glu Pro Arg Asp Pro Ala Val Glu Arg Gln Glu Ala Arg
    130                 135                 140

Cys Ser Tyr Thr Glu Asn Ser Thr Leu Pro Lys Ile Phe Val Thr Lys
145                 150                 155                 160

Asp Ser Asn Thr Met Thr Leu Ala Cys Gly Pro His Gly Ala Pro Met
                165                 170                 175

Pro Glu Ser Tyr Thr Glu Asn Tyr Cys Ser Thr Pro Asp Thr Cys Asp
            180                 185                 190

-continued

```
Glu Lys Pro Phe Thr Ser Val Ile Pro Gly Tyr Leu Ser Lys Trp Phe
        195                 200                 205

Phe Gly Asp Pro Lys Ser Pro Leu Gly Ala Arg Val Arg Ile Pro Pro
        210                 215                 220

Glu Gln Ile Pro Ser Ser Pro Gln Ile Asn Tyr Phe Gly Cys Thr Gly
225                     230                 235                 240

Pro Thr Glu Gly Glu Gly Pro Lys Tyr Asn Cys Thr Val Pro Val Pro
                245                 250                 255

Leu Gly Gly Gly Asp Pro Ser Glu Gly Ser Arg Pro Gly Gly Gly Ser
                260                 265                 270

Gly Gly Gly Lys Arg Gly Gly Gly Gln Gly Gly Gly Gly Ser Leu Ala
        275                 280                 285

Gly Phe Asp Phe Arg Gln Gly Ser
290                     295
```